United States Patent [19]
Lehrer et al.

[11] Patent Number: 6,010,876
[45] Date of Patent: Jan. 4, 2000

[54] CLAVANINS

[75] Inventors: Robert I. Lehrer, Santa Monica; Sylvia L. Harwig, deceased, late of Woodland Hills, by John Harwig, executor; Chengquan Zhao, Los Angeles, all of Calif.; In-Hee Lee, Seoul, Rep. of Korea

[73] Assignee: The Regents of the University of California, Oakland, Calif.

[21] Appl. No.: 08/746,160

[22] Filed: Nov. 6, 1996

[51] Int. Cl.$^7$ .......................... C12N 15/12; C12N 15/63; C12N 1/21; C07K 14/435
[52] U.S. Cl. .................... 435/69.1; 536/23.5; 435/320.1; 435/325; 435/419; 435/252.3; 530/323; 530/326; 530/332
[58] Field of Search ........................ 536/23.5; 435/320.1, 435/325, 419, 252.3; 530/323, 326, 332

[56] References Cited

FOREIGN PATENT DOCUMENTS

| | | |
|---|---|---|
| 0 403 458 | 12/1990 | European Pat. Off. . |
| 0 472 987 | 3/1992 | European Pat. Off. . |
| 93 11783 | 6/1993 | WIPO . |

OTHER PUBLICATIONS

Cornelissen, B. J. C. et al., "Strategies for Control of Fungal Diseases with Transgenic Plants," *Plant Physiol* 101:709–712 (1993).

Bensch, K. W. et al., "hBD–1; a novel β–defensin from human plasma," *Febs Lett* 368:331 (1995).

Christensen, B. et al., "Channel–forming properties of cecropins and related model compounds incorporated into planar lipid membranes," *Proc Natl Acad Sci USA* 85:5072 (1988).

Diamond, G. et al., "Tracheal antimicrobial peptide, a cysteine–rich peptide from mammalian tracheal mucosa: Peptide isolation and cloning of a cDNA," *Proc Natl Acad Sci USA* 88:3952 (1991).

Duclohier, H. et al., "Antimicrobial peptide magainin I from Xenopus skin forms anion–permeable channels in planar lipid bilayers," *Biophys J* 56:1017 (1989).

Harwig, S. S. L. et al., "Gallinacins: cysteine–rich antimicrobial peptides of chicken leukocytes," *Febs Lett* 342:281 (1994).

Jones, D.E. et al., "Paneth Cells of the Human Small Intestine Express and Antimicrobial Peptide Gene," *J Biol Chem* 267:23216 (1992).

Kokryakov, V. N. et al., "Protegrins: leukocyte antimicrobial peptides that combine features of corticostatic defensins and tachyplesins," *Febs Lett* 231 (1993).

Lehrer, R. I. et al., "DEFENSINS: Antimicrobial and Cytotoxic Peptides of Mammalian Cells," *Ann Rev Immunol* 11:105 (1992).

Nakamura, T. et al., "Tachyplesin, a Class of Antimicrobial Peptide from the Hemocytes of the Horseshoe Crab (Tachypleus tridentatus)," *J Biol Chem* 263:16709–16713 (1988).

Patterson–Delafield, J. et al., "Microbial Cationic Proteins in Rabbit Alveolar Macrophages: a Potential Host Defense Mechanism," *Infect Immun* 30:180 (1980).

Schonwetter, B. S. et al., "Epithelial Antibiotics Induced at Sites of Inflammation," *Science* 267:1645 (1995).

Selsted, M. E. et al., "Purification, Primary Structures, and Antibacterial Activities of β–Defensins, a New Family of Antimicrobia Peptides from Bovine Neutrophils," *J. Biol. Chem* 268:6641.

Terry, A. S. et al., "The cDNA Sequence Coding for Prepro–PGS (Prepro–magainins) and Aspects of the Processing of This Prepro–polypeptide," *J Biol Chem* 263:5745 (1988).

Zasloff, M. et al., "Antimicrobial activity of synthetic magainin peptides and several analogues," *Proc Natl Acad Sci USA* 85:910 (1988).

Zasloff, M., "Magainins, a class of antimicrobial peptides from Xenopus skin: Isolation, characterization of two active forms, and partial cDNA sequence of a precursor," *Proc Natl Acad Sci USA* 84:5449 (1987).

*Primary Examiner*—Rebecca E. Pouty
*Attorney, Agent, or Firm*—Morrison & Foerster LLP

[57] ABSTRACT

Novel microbial peptides called clavanins are of the formula $$X'_1X_2B'_3X_4X_5U_6B_7X_8X_9B_{10}B_{11}X_{12}U_{13}Z_{14}\text{-}X_{15}X_{16}B^*_{17}U_{18}X_{19}U_{20}B_{21}X_{22}X_{23} \quad (1)(\text{SEQ ID NO: 1})$$

including the salts, esters, amides and acylated forms thereof
  wherein X is a hydrophobic amino acid residue or modified form thereof;
  X' is a small or a hydrophobic amino acid residue or a modified form thereof;
  B is a basic amino acid residue or modified form thereof;
  B' is basic or a polar/large amino acid residue or modified form thereof; and
  B* is a basic or a hydrophobic amino acid residue or a modified form thereof;
  U is a small amino acid residue or modified form thereof;
  Z is a polar/large amino acid residue or modified form thereof.

4 Claims, 14 Drawing Sheets

```
  1  ACAAACAACAGGAAAGATGAAAACAACAATTTGATTCTTCTCATACTGGGACTTGGCAT
                    M  K  T  T  I  L  I  L  L  I  L  G  L  G  I

61  CAATGCAAAATCTCTGGAGGAAAGAAAATCGGAGGAAGAGAAAGTATTCCAATTCCTTGG
      N  A  K  S  L  E  E  R  K  S  E  E  E  K  V  F  Q  F  L  G

121  CAAAATTATTCATCATGTTGGCAATTTGTACATGGTTTTAGCCACGTGTTCGGCGACGA
      K  I  I  H  H  V  G  N  F  V  H  G  F  S  H  V  F  G  D  D

181  CCAACAAGATAATGGAAAGTTTTATGGCCACTACGCAGAAGACAATGGCAAGCATTGGTA
      Q  Q  D  N  G  K  F  Y  G  H  Y  A  E  D  N  G  K  H  W  Y

241  TGATACCGGGGATCAATAAAAAAAGTTTTAAACAGCTACGCGACTTGAAGACGGACGGACC
      D  T  G  D  Q  *  *  *

301  CGGCAGAACATTGATATTTCTTGTTTCTTTGATTAAAGGCTAGCCTTATTACTCAGAAT
```

FIG.3A

```
  1  CAAACTCAGACAACAACAGGAAACAGGAAAAGATGAAAACAACAATTTGATTCTTCTCATACTGGG
                                  M  K  T  T  I  L  L  I  L  G

61  ACTTGGCATCAATGCAAATCTCTGGAGGAAGAAATCGGAGGAAGAAAAAGTATTCCA
      L  G  I  N  A  K  S  L  E  E  E  R  K  S  E  E  E  K  V  F  H

121  TCTCCCTTGGCAAATTATTCATCATGTTGGCAATTTTGTATATGGTTTTAGCCACGTGTT
      L  L  G  K  I  I  H  H  V  G  N  F  V  Y  G  F  S  H  V  F

181  CGGGCGACGACCAACAAGATAATGGAAAGTTTTATGGCCACTACGGCAGAAGACAATGGCAA
      G  D  D  Q  Q  D  N  G  K  F  Y  G  H  Y  A  E  D  N  G  K

241  GCATTGGTATGATACCGGGGATCAATAAAAAAGTTTTAAACAGCTACGCGACTTGAAGAC
      H  W  Y  D  T  G  D  D  Q  ***

301  GGACGGACCCGGCAGAACATTGATATTCTTGTTTTCTTCTTTGATTAAAGGCTAGCCTTATT

361  ACTCAGAATATAACACTACATTGCATTC
```

FIG. 3B

```
1    CAGACAAACAACAGGAAAGATGAAAACAACAATTTGATTCTTCTCATACTGGGACTTGG
                      M  K  T  T  I  L  I  L  L  I  L  G  L  G

61   CATCAATGCAAAATCTCTGGAGGAAGAAATCGGAGGAAGAGAAAGCTTTCAAACTCCT
      I  N  A  K  S  L  E  E  R  K  S  E  E  E  K  A  F  K  L  L

121  TGGCAGAATTATTCATCATGTTGGCAATTTTGTATATGGTTTTAGCCACGTGTTCGGCGA
      G  R  I  I  H  H  V  G  N  F  V  Y  G  F  S  H  V  F  G  D

181  CGACCAACAAGATAATGGAAAGTTTTATGGCCACTACGCAGAAGACAATGGCAAGCATTG
      D  Q  Q  D  N  G  K  F  Y  G  H  Y  A  E  D  N  G  K  H  W

241  GTATGATACCGGGGATCAATAAAAAAGTTTTAAACAGCTACGCGACTTGAAGACGGACGG
      Y  D  T  G  D  D  Q  *  *  *

301  ACCCGGCAGAACATTGATATTTCTTGTTTTCTTTGATTAAAGGCTAGCCCTTATTAC
```

FIG. 3C

```
1   CAAACTCAGACAACAACAGGAAAGATGAAAACAACAATTTGATTCTTCTCATACTGGG
                              M  K  T  T  T  I  L  L  L  I  L  G

61  ACTTGGCATCAATGCAAAATCTCTGGAGGAAAGAAATCGGAGGAAGAGAAATTATTCAA
    L  G  I  N  A  K  S  L  E  E  R  K  S  E  E  E  K  L  F  K

121 ACTCCCTGGCAAAATTATTCATCATGTTGGCAATTTTGTACATGGTTTTAGCCACGTGTT
    L  L  G  K  I  I  H  H  V  G  N  F  V  H  G  F  S  H  V  F

181 CGGCGACGACCAACAAGATAATGGAAAGTTTTATGGCTACTACGCAGAAGACAATGGCAA
    G  D  D  Q  Q  D  N  G  K  F  Y  G  Y  Y  A  E  D  N  G  K

241 GCATTGGTATGATACCGGGGATCAATAAAAAAAGTTTTAAACAGCTACGCGACTTGAAGAC
    H  W  Y  D  T  G  D  Q  * * *

301 GGACGGACCCC GG
```

FIG.3D

SIGNAL SEQUENCE AND ANIONIC PROPIECE

```
CLAV_A    MKTTILILILGLGINAKSLEERKSEEEK
          ||||||||||||||||||||||||||||
CLAV_C    MKTTILILILGLGINAKSLEERKSEEEK
          ||||||||||||||||||||||||||||
CLAV_D    MKTTILILILGLGINAKSLEERKSEEEK
          ||||||||||||||||||||||||||||
CLAV_E    MKTTILILILGLGINAKSLEERKSEEEK
```

MATURE PEPTIDE AND ANIONIC POSTPIECE

```
CLAV_A    VFQFLGKIIHHVGNFVHGFSHVFGDDQQDNGKFYGHYAEDNGKHWYDTGDQ
          |..||||||||||||||||||||||||||||||||||||||||||||||||
CLAV_C    VFHLLGKIIHHVGNFVYGFSHVFGDDQQDNGKFYGHYAEDNGKHWYDTGDQ
          .|.||||||||||||||||||||||||||||||||||||||||||||||||
CLAV_D    AFKLLGRIIHHVGNFVYGFSHVFGDDQQDNGKFYGHYAEDNGKHWYDTGDQ
          .|.||||||||||||||||||||||||||||||||.|.|||||||||||||
CLAV_E    LFKLLGKIIHHVGNFVHGFSHVFGDDQQDNGKFYGYYAEDNGKHWYDTGDQ
```

FIG.3E

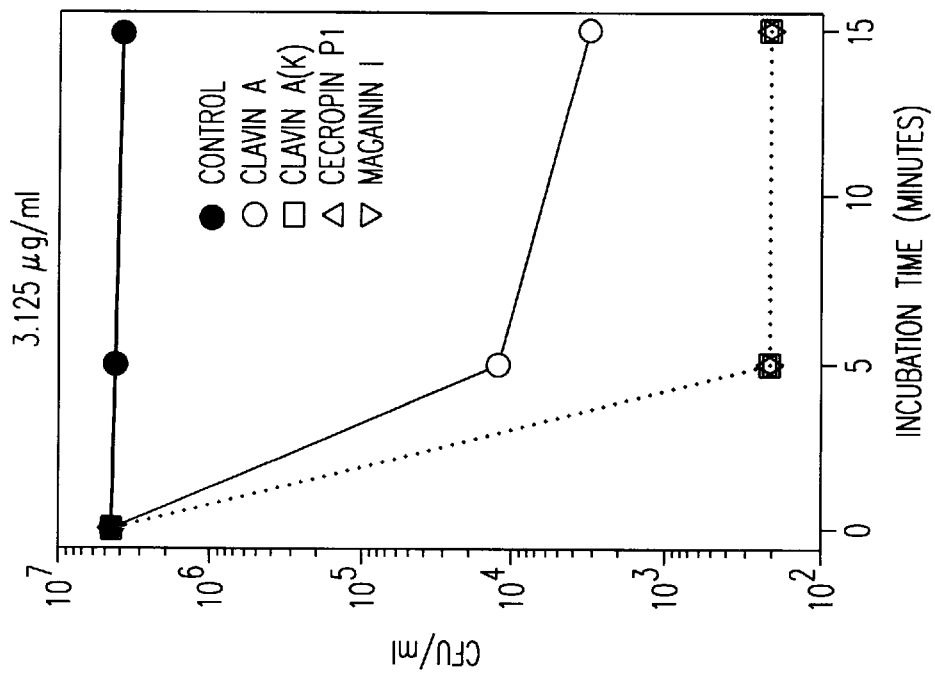
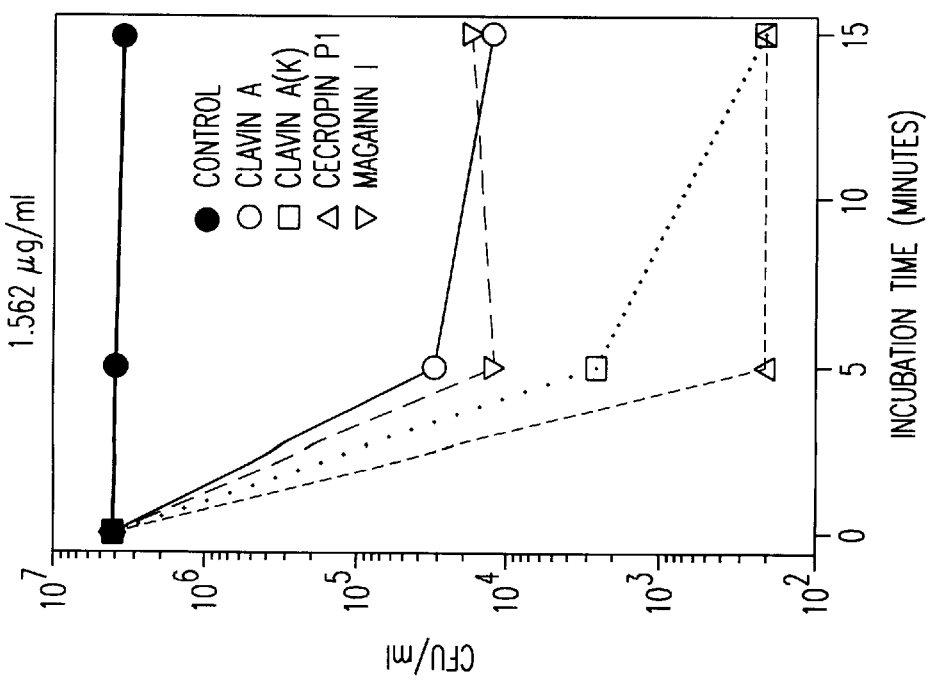
FIG.10B
FIG.10A

SEQUENCE LISTING (1) GENERAL INFORMATION:

(iii) NUMBER OF SEQUENCES: 51

(2) INFORMATION FOR SEQ ID NO:1:

(i) SEQUENCE CHARACTERISTICS:
       (A) LENGTH: 23 amino acids
       (B) TYPE: amino acid
       (C) STRANDEDNESS: single
       (D) TOPOLOGY: linear (ix) FEATURE:

(xi) SEQUENCE DESCRIPTION: SEQ ID NO:1:

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa
            20

(2) INFORMATION FOR SEQ ID NO:2:

(i) SEQUENCE CHARACTERISTICS:
       (A) LENGTH: 360 base pairs
       (B) TYPE: nucleic acid
       (C) STRANDEDNESS: single
       (D) TOPOLOGY: linear (ix) FEATURE:
       (A) NAME/KEY: Coding Sequence
       (B) LOCATION: 17...256
       (D) OTHER INFORMATION:

(xi) SEQUENCE DESCRIPTION: SEQ ID NO:2:

ACAAACAACA GGAAAG ATG AAA ACA ACA ATT TTG ATT CTT CTC ATA CTG GGA    52
                Met Lys Thr Thr Ile Leu Ile Leu Leu Ile Leu Gly
                 1               5                  10

CTT GGC ATC AAT GCA AAA TCT CTG GAG GAA AGA AAA TCG GAG GAA GAG     100
Leu Gly Ile Asn Ala Lys Ser Leu Glu Glu Arg Lys Ser Glu Glu Glu
            15                  20                  25

AAA GTA TTC CAA TTC CTT GGC AAA ATT ATT CAT CAT GTT GGC AAT TTT    148
Lys Val Phe Gln Phe Leu Gly Lys Ile Ile His His Val Gly Asn Phe
    30                  35                  40

GTA CAT GGT TTT AGC CAC GTG TTC GGC GAC GAC CAA CAA GAT AAT GGA    196
Val His Gly Phe Ser His Val Phe Gly Asp Asp Gln Gln Asp Asn Gly
45                  50                  55                  60

AAG TTT TAT GGC CAC TAC GCA GAA GAC AAT GGC AAG CAT TGG TAT GAT    244
Lys Phe Tyr Gly His Tyr Ala Glu Asp Asn Gly Lys His Trp Tyr Asp
                65                  70                  75

ACC GGG GAT CAA TAAAAAAGTT TTAAACAGCT ACGCGACTTG AAGACGGACG GACCC  301
Thr Gly Asp Gln
            80

GGCAGAACAT TGATATTTCT TGTTTTCTTT GATTAAAGGC TAGCCTTATT ACTCAGAAT    360

(2) INFORMATION FOR SEQ ID NO:3:

(i) SEQUENCE CHARACTERISTICS:
       (A) LENGTH: 80 amino acids
       (B) TYPE: amino acid
       (C) STRANDEDNESS: single
       (D) TOPOLOGY: linear (ii) MOLECULE TYPE: protein (v) FRAGMENT TYPE: internal (xi) SEQUENCE DESCRIPTION: SEQ ID NO:3:

```
Met Lys Thr Thr Ile Leu Ile Leu Leu Ile Leu Gly Leu Gly Ile Asn
1               5                   10                  15

Ala Lys Ser Leu Glu Glu Arg Lys Ser Glu Glu Lys Val Phe Gln
            20                  25                  30

Phe Leu Gly Lys Ile Ile His His Val Gly Asn Phe Val His Gly Phe
        35                  40                  45

Ser His Val Phe Gly Asp Asp Gln Gln Asp Asn Gly Lys Phe Tyr Gly
    50                  55                  60

His Tyr Ala Glu Asp Asn Gly Lys His Trp Tyr Asp Thr Gly Asp Gln
65                  70                  75                  80
```

(2) INFORMATION FOR SEQ ID NO:4:

(i) SEQUENCE CHARACTERISTICS:
        (A) LENGTH: 388 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 26...265
        (D) OTHER INFORMATION:

(xi) SEQUENCE DESCRIPTION: SEQ ID NO:4:

```
CAAACTCAGA CAAACAACAG GAAAG ATG AAA ACA ACA ATT TTG ATT CTT CTC      52
                            Met Lys Thr Thr Ile Leu Ile Leu Leu
                            1               5

ATA CTG GGA CTT GGC ATC AAT GCA AAA TCT CTG GAG GAA AGA AAA TCG     100
Ile Leu Gly Leu Gly Ile Asn Ala Lys Ser Leu Glu Glu Arg Lys Ser
10                  15                  20                  25

GAG GAA GAA AAA GTA TTC CAT CTC CTT GGC AAA ATT ATT CAT CAT GTT     148
Glu Glu Glu Lys Val Phe His Leu Leu Gly Lys Ile Ile His His Val
                30                  35                  40

GGC AAT TTT GTA TAT GGT TTT AGC CAC GTG TTC GGC GAC GAC CAA CAA     196
Gly Asn Phe Val Tyr Gly Phe Ser His Val Phe Gly Asp Asp Gln Gln
            45                  50                  55

GAT AAT GGA AAG TTT TAT GGC CAC TAC GCA GAA GAC AAT GGC AAG CAT     244
Asp Asn Gly Lys Phe Tyr Gly His Tyr Ala Glu Asp Asn Gly Lys His
        60                  65                  70

TGG TAT GAT ACC GGG GAT CAA TAAAAAAGTT TTAAACAGCT ACGCGACTTG AAGA   299
Trp Tyr Asp Thr Gly Asp Gln
        75              80

CGGACGGACC CGGCAGAACA TTGATATTTC TTGTTTTCTT TGATTAAAGG CTAGCCTTAT   359

TACTCAGAAT ATAACACTAC ATTGCATTC                                     388
```

(2) INFORMATION FOR SEQ ID NO:5:

(i) SEQUENCE CHARACTERISTICS:
        (A) LENGTH: 80 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:5:

```
Met Lys Thr Thr Ile Leu Ile Leu Leu Ile Leu Gly Leu Gly Ile Asn
1               5                   10                  15
```

```
Ala Lys Ser Leu Glu Glu Arg Lys Ser Glu Glu Lys Val Phe His
         20                  25                  30

Leu Leu Gly Lys Ile Ile His His Val Gly Asn Phe Val Tyr Gly Phe
         35                  40                  45

Ser His Val Phe Gly Asp Asp Gln Gln Asp Asn Gly Lys Phe Tyr Gly
     50                  55                  60

His Tyr Ala Glu Asp Asn Gly Lys His Trp Tyr Asp Thr Gly Asp Gln
65                  70                  75                  80

(2) INFORMATION FOR SEQ ID NO:6:

(i) SEQUENCE CHARACTERISTICS:
        (A) LENGTH: 356 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 20...259
        (D) OTHER INFORMATION:

(xi) SEQUENCE DESCRIPTION: SEQ ID NO:6:

CAGACAAACA ACAGGAAAG ATG AAA ACA ACA ATT TTG ATT CTT CTC ATA CTG       52
                    Met Lys Thr Thr Ile Leu Ile Leu Leu Ile Leu
                     1               5                      10

GGA CTT GGC ATC AAT GCA AAA TCT CTG GAG GAA AGA AAA TCG GAG GAA       100
Gly Leu Gly Ile Asn Ala Lys Ser Leu Glu Glu Arg Lys Ser Glu Glu
             15                  20                  25

GAG AAA GCT TTC AAA CTC CTT GGC AGA ATT ATT CAT CAT GTT GGC AAT       148
Glu Lys Ala Phe Lys Leu Leu Gly Arg Ile Ile His His Val Gly Asn
         30                  35                  40

TTT GTA TAT GGT TTT AGC CAC GTG TTC GGC GAC GAC CAA CAA GAT AAT       196
Phe Val Tyr Gly Phe Ser His Val Phe Gly Asp Asp Gln Gln Asp Asn
     45                  50                  55

GGA AAG TTT TAT GGC CAC TAC GCA GAA GAC AAT GGC AAG CAT TGG TAT       244
Gly Lys Phe Tyr Gly His Tyr Ala Glu Asp Asn Gly Lys His Trp Tyr
60                  65                  70                  75

GAT ACC GGG GAT CAA TAAAAAAGTT TTAAACAGCT ACGCGACTTG AAGACGGACG G    300
Asp Thr Gly Asp Gln
             80

ACCCGGCAGA ACATTGATAT TTCTTGTTTT CTTTGATTAA AGGCTAGCCT TATTAC        356

(2) INFORMATION FOR SEQ ID NO:7:

(i) SEQUENCE CHARACTERISTICS:
        (A) LENGTH: 80 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:7:

Met Lys Thr Thr Ile Leu Ile Leu Leu Ile Leu Gly Leu Gly Ile Asn
 1               5                  10                  15

Ala Lys Ser Leu Glu Glu Arg Lys Ser Glu Glu Lys Ala Phe Lys
         20                  25                  30

Leu Leu Gly Arg Ile Ile His His Val Gly Asn Phe Val Tyr Gly Phe
         35                  40                  45

Ser His Val Phe Gly Asp Asp Gln Gln Asp Asn Gly Lys Phe Tyr Gly
     50                  55                  60
```

```
His Tyr Ala Glu Asp Asn Gly Lys His Trp Tyr Asp Thr Gly Asp Gln
 65                  70                  75                  80
```

(2) INFORMATION FOR SEQ ID NO:8:

(i) SEQUENCE CHARACTERISTICS:
        (A) LENGTH: 312 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 26...265
        (D) OTHER INFORMATION:

(xi) SEQUENCE DESCRIPTION: SEQ ID NO:8:

```
CAAACTCAGA CAAACAACAG GAAAG ATG AAA ACA ACA ATT TTG ATT CTT CTC        52
                            Met Lys Thr Thr Ile Leu Ile Leu Leu
                             1               5

ATA CTG GGA CTT GGC ATC AAT GCA AAA TCT CTG GAG GAA AGA AAA TCG       100
Ile Leu Gly Leu Gly Ile Asn Ala Lys Ser Leu Glu Glu Arg Lys Ser
 10              15                  20                  25

GAG GAA GAG AAA TTA TTC AAA CTC CTT GGC AAA ATT ATT CAT CAT GTT       148
Glu Glu Glu Lys Leu Phe Lys Leu Leu Gly Lys Ile Ile His His Val
                 30                  35                  40

GGC AAT TTT GTA CAT GGT TTT AGC CAC GTG TTC GGC GAC GAC CAA CAA       196
Gly Asn Phe Val His Gly Phe Ser His Val Phe Gly Asp Asp Gln Gln
             45                  50                  55

GAT AAT GGA AAG TTT TAT GGC TAC TAC GCA GAA GAC AAT GGC AAG CAT       244
Asp Asn Gly Lys Phe Tyr Gly Tyr Tyr Ala Glu Asp Asn Gly Lys His
         60                  65                  70

TGG TAT GAT ACC GGG GAT CAA TAAAAAAGTT TTAAACAGCT ACGCGACTTG AAGA     299
Trp Tyr Asp Thr Gly Asp Gln
 75              80

CGGACGGACC CGG                                                        312
```

(2) INFORMATION FOR SEQ ID NO:9:

(i) SEQUENCE CHARACTERISTICS:
        (A) LENGTH: 80 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:9:

```
Met Lys Thr Thr Ile Leu Ile Leu Leu Ile Leu Gly Leu Gly Ile Asn
 1               5                  10                  15

Ala Lys Ser Leu Glu Glu Arg Lys Ser Glu Glu Lys Leu Phe Lys
                 20                  25                  30

Leu Leu Gly Lys Ile Ile His His Val Gly Asn Phe Val His Gly Phe
             35                  40                  45

Ser His Val Phe Gly Asp Asp Gln Gln Asp Asn Gly Lys Phe Tyr Gly
         50                  55                  60

Tyr Tyr Ala Glu Asp Asn Gly Lys His Trp Tyr Asp Thr Gly Asp Gln
 65                  70                  75                  80
```

(2) INFORMATION FOR SEQ ID NO:10:

```
        (i) SEQUENCE CHARACTERISTICS:
            (A) LENGTH: 23 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 20...20
            (D) OTHER INFORMATION: D-Ser (xi) SEQUENCE DESCRIPTION: SEQ ID NO:10:

Val Phe Asn Phe Leu Gly Lys Ile Ile His His Val Gly Asn Phe Val
 1               5                  10                  15

Lys Gly Phe Xaa His Val Phe
            20

(2) INFORMATION FOR SEQ ID NO:11:

(i) SEQUENCE CHARACTERISTICS:
            (A) LENGTH: 23 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 10...10
            (D) OTHER INFORMATION: D-His (xi) SEQUENCE DESCRIPTION: SEQ ID NO:11:

Ile Phe Gln Phe Leu Gly Lys Ile Ile Xaa Lys Val Gly Asn Phe Ile
 1               5                  10                  15

His Gly Phe Ser Lys Val Phe
            20

(2) INFORMATION FOR SEQ ID NO:12:

(i) SEQUENCE CHARACTERISTICS:
            (A) LENGTH: 23 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:12:

Val Phe His Phe Leu Gly Lys Ile Ile His His Val Gly Asn Phe Val
 1               5                  10                  15

Lys Gly Phe Ser His Val Phe
            20

(2) INFORMATION FOR SEQ ID NO:13:

(i) SEQUENCE CHARACTERISTICS:
            (A) LENGTH: 23 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:13:

Val Phe Gln Phe Leu Gly Lys Ile Ile Lys His Val Gly Asn Phe Leu
 1               5                  10                  15
```

His Gly Phe Ser His Val Phe
            20

(2) INFORMATION FOR SEQ ID NO:14:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:14:

Val Phe Lys Phe Leu Gly Lys Ile Val His Lys Val Gly Asn Phe Val
1               5                   10                  15

Lys Gly Phe Ser Arg Val Phe
            20

(2) INFORMATION FOR SEQ ID NO:15:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 5...5
        (D) OTHER INFORMATION: D-Leu
        (A) NAME/KEY: Other
        (B) LOCATION: 10...10
        (D) OTHER INFORMATION: D-His (xi) SEQUENCE DESCRIPTION: SEQ ID NO:15:

Leu Phe Gln Phe Xaa Gly Lys Ile Ile Xaa His Val Gly Asn Phe Ile
1               5                   10                  15

His Gly Phe Ser His Val Tyr
            20

(2) INFORMATION FOR SEQ ID NO:16:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:16:

Val Phe Gln Phe Leu Gly Lys Leu Ile His His Val Gly Asn Phe Val
1               5                   10                  15

His Gly Phe Ser Lys Val Phe
            20

(2) INFORMATION FOR SEQ ID NO:17:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None

```
       (xi) SEQUENCE DESCRIPTION: SEQ ID NO:17:

Ile Phe Gln Phe Leu Gly Lys Ile Val His Lys Val Gly Gln Phe Leu
1               5                   10                  15

His Gly Phe Ser Lys Val Phe
            20

(2) INFORMATION FOR SEQ ID NO:18:

(i) SEQUENCE CHARACTERISTICS:
           (A) LENGTH: 23 amino acids
           (B) TYPE: amino acid
           (C) STRANDEDNESS: single
           (D) TOPOLOGY: linear (ii) MOLECULE TYPE: None (xi) SEQUENCE DESCRIPTION: SEQ ID NO:18:

Val Phe Arg Phe Leu Gly Lys Ile Val His His Val Gly Asn Phe Val
1               5                   10                  15

Arg Gly Phe Ser His Val Phe
            20

(2) INFORMATION FOR SEQ ID NO:19:

(i) SEQUENCE CHARACTERISTICS:
           (A) LENGTH: 23 amino acids
           (B) TYPE: amino acid
           (C) STRANDEDNESS: single
           (D) TOPOLOGY: linear (ii) MOLECULE TYPE: None (xi) SEQUENCE DESCRIPTION: SEQ ID NO:19:

Ser Phe Gln Phe Leu Gly Lys Ile Ile Lys His Val Gly Asn Phe Leu
1               5                   10                  15

Lys Gly Tyr Ser Arg Val Phe
            20

(2) INFORMATION FOR SEQ ID NO:20:

(i) SEQUENCE CHARACTERISTICS:
           (A) LENGTH: 23 amino acids
           (B) TYPE: amino acid
           (C) STRANDEDNESS: single
           (D) TOPOLOGY: linear (ii) MOLECULE TYPE: None (ix) FEATURE:
           (A) NAME/KEY: Other
           (B) LOCATION: 7...7
           (D) OTHER INFORMATION: D-Lys
           (A) NAME/KEY: Other
           (B) LOCATION: 14...14
           (D) OTHER INFORMATION: D-Asn (xi) SEQUENCE DESCRIPTION: SEQ ID NO:20:

Val Phe Gln Phe Leu Gly Xaa Ile Leu His His Val Gly Xaa Phe Val
1               5                   10                  15

His Ser Phe Ser His Leu Phe
            20

(2) INFORMATION FOR SEQ ID NO:21:

(i) SEQUENCE CHARACTERISTICS:
           (A) LENGTH: 23 amino acids
           (B) TYPE: amino acid
           (C) STRANDEDNESS: single
```

(D) TOPOLOGY: linear (ii) MOLECULE TYPE: None (ix) FEATURE:
            (A) NAME/KEY: Other
            (B) LOCATION: 20...20
            (D) OTHER INFORMATION: D-Ser (xi) SEQUENCE DESCRIPTION: SEQ ID NO:21:

Val Phe Lys Phe Leu Gly Lys Ile Ile Arg Lys Val Gly Asn Phe Val
 1               5                  10                  15

His Ala Phe Xaa Lys Val Phe
            20

(2) INFORMATION FOR SEQ ID NO:22:

(i) SEQUENCE CHARACTERISTICS:
            (A) LENGTH: 23 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:22:

Ala Phe Gln Phe Leu Gly Lys Ile Leu Lys Arg Val Gly Asn Phe Leu
 1               5                  10                  15

Lys Gly Phe Ser His Val Tyr
            20

(2) INFORMATION FOR SEQ ID NO:23:

(i) SEQUENCE CHARACTERISTICS:
            (A) LENGTH: 23 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 14...14
            (D) OTHER INFORMATION: D-Asn (xi) SEQUENCE DESCRIPTION: SEQ ID NO:23:

Val Phe Gln Phe Leu Gly Lys Ile Ile Lys His Val Gly Xaa Phe Val
 1               5                  10                  15

His Gly Phe Ser Arg Val Phe
            20

(2) INFORMATION FOR SEQ ID NO:24:

(i) SEQUENCE CHARACTERISTICS:
            (A) LENGTH: 23 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:24:

Ala Phe Gln Phe Leu Gly Lys Ile Ile His His Val Gly Asn Phe Ile
 1               5                  10                  15

Lys Gly Phe Ser Lys Val Phe
            20

(2) INFORMATION FOR SEQ ID NO:25:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 9...9
        (D) OTHER INFORMATION: D-Ile (xi) SEQUENCE DESCRIPTION: SEQ ID NO:25:

Val Phe Lys Phe Leu Gly Lys Val Xaa His His Val Gly Gln Phe Val
1              5                    10                15

His Gly Phe Ser His Val Phe
          20

(2) INFORMATION FOR SEQ ID NO:26:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 5...5
        (D) OTHER INFORMATION: D-Leu (xi) SEQUENCE DESCRIPTION: SEQ ID NO:26:

Val Phe Gln Phe Xaa Gly Lys Ile Ile Lys His Val Ala Gln Phe Leu
1              5                    10                15

His Gly Phe Ser Arg Val Phe
          20

(2) INFORMATION FOR SEQ ID NO:27:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:27:

Val Phe His Phe Leu Gly Lys Ile Ile His His Val Gly Asn Phe Val
1              5                    10                15

Lys Gly Phe Ser His Val Trp
          20

(2) INFORMATION FOR SEQ ID NO:28:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 3...3

(D) OTHER INFORMATION: D-Gln (xi) SEQUENCE DESCRIPTION: SEQ ID NO:28:

Ile Phe Xaa Phe Leu Gly Lys Ile Leu Lys Leu Val Gly Asn Phe Val
 1               5                  10                  15

His Gly Phe Gly His Val Phe
            20

(2) INFORMATION FOR SEQ ID NO:29:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:29:

Val Phe Gln Phe Leu Gly Lys Ile Ile His Lys Val Gly Asn Tyr Val
 1               5                  10                  15

Arg Gly Phe Ser Lys Val Phe
            20

(2) INFORMATION FOR SEQ ID NO:30:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:30:

Gly Phe Lys Phe Leu Gly Lys Val Ile His His Val Ala Asn Trp Leu
 1               5                  10                  15

His Gly Phe Ser Lys Val Phe
            20

(2) INFORMATION FOR SEQ ID NO:31:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:31:

Leu Phe Gln Phe Leu Gly Lys Ile Ile Lys His Val Ser Asn Phe Val
 1               5                  10                  15

Lys Gly Phe Ser His Val Phe
            20

(2) INFORMATION FOR SEQ ID NO:32:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:32:

```
Val Phe Arg Phe Leu Gly Lys Ile Ile Lys Lys Val Gly Asn Phe Val
 1               5                  10                  15

His Gly Phe Ala Lys Val Phe
                20
```

(2) INFORMATION FOR SEQ ID NO:33:

(i) SEQUENCE CHARACTERISTICS:
       (A) LENGTH: 23 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO:33:

```
Ser Phe Gln Phe Leu Gly Lys Ile Ile Arg Lys Val Gly Gln Phe Ile
 1               5                  10                  15

His Gly Phe Gly His Val Phe
                20
```

(2) INFORMATION FOR SEQ ID NO:34:

(i) SEQUENCE CHARACTERISTICS:
       (A) LENGTH: 23 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO:34:

```
Val Phe Gln Phe Leu Gly Lys Ile Val His Lys Val Ala Asn Phe Leu
 1               5                  10                  15

His Gly Phe Ser His Val Trp
                20
```

(2) INFORMATION FOR SEQ ID NO:35:

(i) SEQUENCE CHARACTERISTICS:
       (A) LENGTH: 23 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO:35:

```
Val Phe Asn Phe Leu Gly Lys Ile Ile Arg Arg Val Gly Asn Phe Val
 1               5                  10                  15

Lys Gly Phe Ser Arg Val Phe
                20
```

(2) INFORMATION FOR SEQ ID NO:36:

(i) SEQUENCE CHARACTERISTICS:
       (A) LENGTH: 23 amino acids
       (B) TYPE: amino acid
       (C) STRANDEDNESS: single
       (D) TOPOLOGY: linear (ii) MOLECULE TYPE: None (ix) FEATURE:
       (A) NAME/KEY: Other
       (B) LOCATION: 15...15
       (D) OTHER INFORMATION: D-Phe (xi) SEQUENCE DESCRIPTION: SEQ ID NO:36:

```
Ala Phe Lys Phe Leu Gly Lys Leu Ile His His Val Gly Asn Xaa Ile
  1               5                  10                  15

His Gly Phe Gly His Val Tyr
              20

(2) INFORMATION FOR SEQ ID NO:37:

(i) SEQUENCE CHARACTERISTICS:
         (A) LENGTH: 23 amino acids
         (B) TYPE: amino acid
         (C) STRANDEDNESS: single
         (D) TOPOLOGY: linear (ii) MOLECULE TYPE: None (xi) SEQUENCE DESCRIPTION: SEQ ID NO:37:

Val Phe Gln Phe Leu Gly Lys Ile Ile Arg Lys Val Gly Asn Phe Val
  1               5                  10                  15

Lys Gly Phe Ser Lys Val Tyr
              20

(2) INFORMATION FOR SEQ ID NO:38:

(i) SEQUENCE CHARACTERISTICS:
         (A) LENGTH: 23 amino acids
         (B) TYPE: amino acid
         (C) STRANDEDNESS: single
         (D) TOPOLOGY: linear (ii) MOLECULE TYPE: None (ix) FEATURE:
         (A) NAME/KEY: Other
         (B) LOCATION: 7...7
         (D) OTHER INFORMATION: D-Lys (xi) SEQUENCE DESCRIPTION: SEQ ID NO:38:

Val Phe Asn Phe Leu Gly Xaa Ile Ile His Lys Val Gly Asn Phe Val
  1               5                  10                  15

His Gly Phe Ser Lys Val Phe
              20

(2) INFORMATION FOR SEQ ID NO:39:

(i) SEQUENCE CHARACTERISTICS:
         (A) LENGTH: 23 amino acids
         (B) TYPE: amino acid
         (C) STRANDEDNESS: single
         (D) TOPOLOGY: linear (ii) MOLECULE TYPE: None (ix) FEATURE:
         (A) NAME/KEY: Other
         (B) LOCATION: 11...11
         (D) OTHER INFORMATION: D-His (xi) SEQUENCE DESCRIPTION: SEQ ID NO:39:

Ala Phe Gln Phe Leu Gly Lys Ile Val His Xaa Val Gly Asn Phe Leu
  1               5                  10                  15

His Gly Phe Ala His Val Trp
              20

(2) INFORMATION FOR SEQ ID NO:40:

(i) SEQUENCE CHARACTERISTICS:
         (A) LENGTH: 23 amino acids
         (B) TYPE: amino acid
```

(C) STRANDEDNESS: single
        (D) TOPOLOGY: linear (ii) MOLECULE TYPE: None (xi) SEQUENCE DESCRIPTION: SEQ ID NO:40:

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

(2) INFORMATION FOR SEQ ID NO:41:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:41:

Gly Ile Gly Lys Phe Leu His Ser Ala Gly Lys Phe Gly Lys Ala Phe
1               5                   10                  15

Val Gly Glu Ile Met Lys Ser
            20

(2) INFORMATION FOR SEQ ID NO:42:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:42:

Gly Ile Gly Lys Phe Leu Lys Ser Ala Gly Lys Phe Gly Lys Ala Phe
1               5                   10                  15

Val Asn Glu Ile Met Lys Ser
            20

(2) INFORMATION FOR SEQ ID NO:43:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:43:

Val Phe Gln Phe Leu Gly Lys Ile Ile His His Val Gly Asn Phe Val
1               5                   10                  15

His Gly Phe Ser His Val Phe
            20

(2) INFORMATION FOR SEQ ID NO:44:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:44:

Val Phe Gln Phe Leu Gly Arg Ile Ile His His Val Gly Asn Phe Val
1               5                   10                  15

His Gly Phe Ser His Val Phe
            20

(2) INFORMATION FOR SEQ ID NO:45:

(i) SEQUENCE CHARACTERISTICS:
            (A) LENGTH: 23 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 17...17
            (D) OTHER INFORMATION: o-methyl tyrosine (xi) SEQUENCE DESCRIPTION: SEQ ID NO:45:

Val Phe His Leu Leu Gly Lys Ile Ile His His Val Gly Asn Phe Val
1               5                   10                  15

Tyr Gly Phe Ser His Val Phe
            20

(2) INFORMATION FOR SEQ ID NO:46:

(i) SEQUENCE CHARACTERISTICS:
            (A) LENGTH: 23 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 17...17
            (D) OTHER INFORMATION: o-methyl tyrosine (xi) SEQUENCE DESCRIPTION: SEQ ID NO:46:

Ala Phe Lys Leu Leu Gly Arg Ile Ile His His Val Gly Asn Phe Val
1               5                   10                  15

Tyr Gly Phe Ser His Val Phe
            20

(2) INFORMATION FOR SEQ ID NO:47:

(i) SEQUENCE CHARACTERISTICS:
            (A) LENGTH: 23 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:47:

Leu Phe Lys Leu Leu Gly Lys Ile Ile His His Val Gly Asn Phe Val
1               5                   10                  15

His Gly Phe Ser His Val Phe
            20

(2) INFORMATION FOR SEQ ID NO:48:

(i) SEQUENCE CHARACTERISTICS:

```
            (A) LENGTH: 15 amino acids
            (B) TYPE: amino acid
            (C) STRANDEDNESS: single
            (D) TOPOLOGY: linear (ix) FEATURE:
            (A) NAME/KEY: Other
            (B) LOCATION: 8...8
            (D) OTHER INFORMATION: o-methyl tyrosine (xi) SEQUENCE DESCRIPTION: SEQ ID NO:48:

His His Val Gly Asn Phe Val Tyr Gly Phe Ser His Val Phe Gly
 1               5                  10                  15

(2) INFORMATION FOR SEQ ID NO:49:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ix) FEATURE:
            (A) NAME/KEY: Modified Base
            (B) LOCATION: 19...19
            (D) OTHER INFORMATION: inosine
            (A) NAME/KEY: Modified Base
            (B) LOCATION: 22...22
            (D) OTHER INFORMATION: inosine (xi) SEQUENCE DESCRIPTION: SEQ ID NO:49:

GTCGACTAGT CAYCAYGTNG GNAAYTTYGT                                    30

(2) INFORMATION FOR SEQ ID NO:50:

(i) SEQUENCE CHARACTERISTICS:
            (A) LENGTH: 7 amino acids
            (B) TYPE: amino acid
            (C) STRANDEDNESS: single
            (D) TOPOLOGY: linear (xi) SEQUENCE DESCRIPTION: SEQ ID NO:50:

His His Val Gly Asn Phe Val
 1               5

(2) INFORMATION FOR SEQ ID NO:51:

(i) SEQUENCE CHARACTERISTICS:
            (A) LENGTH: 11 amino acids
            (B) TYPE: amino acid
            (C) STRANDEDNESS: single
            (D) TOPOLOGY: linear (xi) SEQUENCE DESCRIPTION: SEQ ID NO:51:

Ser Leu Glu Glu Arg Lys Ser Glu Glu Glu Lys
 1               5                  10
```

CLAVANINS

ACKNOWLEDGMENT OF GOVERNMENT SUPPORT

This invention was made at least in part with funding from NIH grant numbers 1-PO1-AI-37945-01 and 5R37-AI-22839-10. The U.S. Government has certain rights in this invention.

TECHNICAL FIELD

The invention relates to a class of peptide and peptide-like compounds with antimicrobial activity. These peptides, designated "clavanins" are characterized by patterns of basic and hydrophobic amino acids which result in compounds with a spectrum of antimicrobial activities.

BACKGROUND ART

Antimicrobial peptides have been isolated from a wide variety of animal sources. These sources include, prominently, leukocytes of humans (Lehrer, R. I. et al., *Ann Rev Immunol* (1992) 11:105); pigs (Kokryakov, V. N. et al., *FEBS Lett* (1993) 231); bovine sources (Selsted, M. E. et al., *J Biol Chem* (1993) 268:6641); rabbits (Patterson-Delafield, J. et al., *Infect Immun* (1980) 30:180); and birds (Harwig, S. S. L. et al., *FEBS Lett* (1994) 342:281). Antimicrobial peptides have also been found in bovine tongue (Schonwetter, B. S. et al., *Science* (1995) 267:1645) respiratory tract epithelia (Diamond, G. et al., *Proc Natl Acad Sci USA* (1991) 88:3952) and gastrointestinal and genital urinary tracts of humans and animals (Jones, D. E. et al., *J Biol Chem* (1992) 267:23216; Bensch, K. W. et al., *FEBS Lett* (1995) 368:331). In addition, antimicrobial peptides have been isolated from the hemocytes of the Horseshoe Crab as described by Nakamura, T. et al., *J Biol Chem* (1988) 263:16709–16713. These various antimicrobial peptides, for example the tachyplesins, polyphemusins, defensins, clavanins and gallinacins, are typically characterized by specific positions of cysteine residues which putatively control conformation of the molecule.

An additional class of antimicrobial peptides, found in the skin of the African clawed frog, *Xenopus laevis,* are α-helical (noncovalent-cyclic) peptides (Zasloff, M., *Proc Natl Acad Sci USA* (1987) 84:5449). This class of antimicrobial peptides, called the magainins, in their mature form contain, 23 amino acids and are α-helical but not amidated. The magainins possess broad spectrum antimicrobial activity (Harwig, S. S. L. et al., *FEBS Lett* (1994) 342:281; Zasloff, M. et al., *Proc Natl Acad Sci USA* (1988) 85:910). The nature of the antimicrobial activity as related to the α-helical amphipathic structure of magainins has been studied (Duclohier, H. et al., *Biophys J* (1989) 56:1017) as has that of another class of α-helical antimicrobial peptides, the cecropins (Christensen, B. et al., *Proc Natl Acad Sci USA* (1988) 85:5072. The magainins are synthesized from a large prepropeptide containing a single copy of Magainin-1 and five copies of the closely related Magainin-2 (Terry, A. S. et al., *J Biol Chem* (1988) 263:5745).

Antimicrobial peptides and proteins have also been found in plants as reviewed by Cornelissen, B. J. C. et al., *Plant Physiol* (1993) 101:709–712.

The present invention is directed to a class of peptides and peptide-like compounds several members of which may be isolated from the hemocytes of the tunicate *Styela lava.* Tunicates are simple marine invertebrates whose larval forms contain a constellation of features establishing their kinship to early vertebrates. The body cavity of the mature tunicate provides an acceptable source of mesoderm-derived phagocytes (hemocytes) that are counterparts to the blood leukocytes of higher vertebrates. It is known that phagocytes of freshly harvested colonial tunicates are often filled with various bacteria and that the introduction of bacteria beneath the tunic is capable of inducing phagocytic cells to traverse the underlying epithelium and surround these foreign objects.

DISCLOSURE OF THE INVENTION

The invention is directed to a class of peptides and peptide-like compounds, the clavanins, that are characterized by specific patterns of basic and hydrophobic amino acid side-chains and which show a broad spectrum of antimicrobial activity. The clavanins are therefore useful additions to the repertoire of agents useful in preserving materials otherwise susceptible to microbial degradation, in protecting plants against bacterial infection, and in therapeutic and prophylactic protection of animals against bacteria, fungi and viruses. As used in the present application "antimicrobial" refers to the ability to inhibit the growth of, destroy, or otherwise impede the undesired destructive effects of such replicable forms.

Thus, in one aspect, the invention is directed to compounds of the formula (SEQ ID NO: 1):

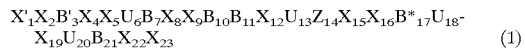

$$X'_1X_2B'_3X_4X_5U_6B_7X_8X_9B_{10}B_{11}X_{12}U_{13}Z_{14}X_{15}X_{16}B^*{}_{17}U_{18}\text{-}X_{19}U_{20}B_{21}X_{22}X_{23} \quad (1)$$

wherein X is a hydrophobic amino acid residue or modified form thereof;

X' is a small or a hydrophobic amino acid residue or a modified form thereof;

B is a basic amino acid residue or modified form thereof;

B' is basic or a polar/large amino acid residue or modified form thereof; and

B* is a basic or a hydrophobic amino acid residue or a modified form thereof;

U is a small amino acid residue or modified form thereof;

Z is a polar/large amino acid residue or modified form thereof.

Included in the invention are the compounds of formula (1) in the acylated and/or amidated form as well as the esters and salts.

In other aspects, the invention is directed to recombinant materials useful for the production of those peptides of the invention that contain gene-encoded amino acids, as well as plants or animals modified to contain expression systems for the production of these peptides. The invention also includes methods to prepare and manipulate these recombinant materials.

In addition, the invention is directed to pharmaceutical compositions and compositions for application to plants and to materials whose preservation from microbial growth is desired, which compositions contain the compounds of the invention as active ingredients and to compositions which contain expression systems for the production of the peptides for in situ expression of the nucleotide sequence encoding these peptides. The invention is also directed to methods to prepare the invention compounds synthetically, to antibodies specific for these compounds, and to the use of the compounds as preservatives, therapeutics, and prophylactics. The invention is also directed to the use of the compounds of the invention as standards in antimicrobial assays and as affinity ligands for adsorption of counterpart structures in microbes, including viruses, as set forth above.

BRIEF DESCRIPTION OF THE DRAWINGS

FIGS. 3A–3E (SEQ ID NO: 2 through SEQ ID NO: 9) show sequences of cDNA encoding clavanins A, C, D and E and a comparison of pre- and post-sequences.

FIG. 10 shows the kinetics of Clavanin A, Clavanin A(K) and comparatively, Cecropin P1 and Magainin 1 in their antimicrobial action against E. coli ML-35P.

MODES OF CARRYING OUT THE INVENTION

Figure 1A:
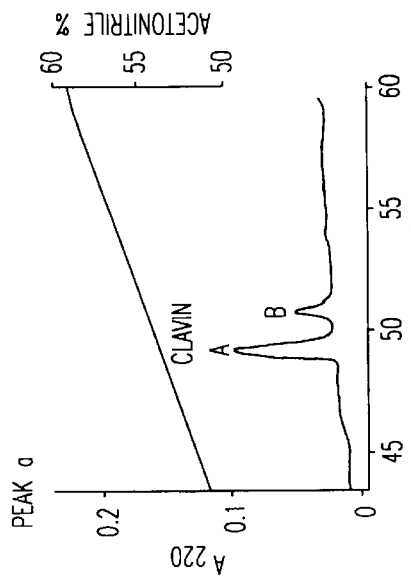
FIG. 1 shows reverse-phase HPLC of the clavanin-containing fraction derived from S. clava hemocytes. The drawing further includes depictions of further separation of peaks a and b derived from an initial chromatographic run.

The compounds of the invention are generally described by the formula $$X'_1X_2B'_3X_4X_5U_6B_7X_8X_9B_{10}B_{11}X_{12}U_{13}Z_{14}X_{15}X_{16}B^*_{17}U_{18}-X_{19}U_{20}B_{21}X_{22}X_{23} \quad (1)$$

and the salts, esters, amides, and acyl forms thereof. Each position represented by a letter indicates a single amino acid residue although, as described below, one or more of the peptide linkages between such residues may be replaced by a peptide linkage mimic. The invention compounds include those represented by formula (1) as well as analogous peptides which are isolatable from the hemocytes of tunicates. "Analogous" forms are those which retain the ability to form an α-helical configuration, are antimicrobial, and are linear (rather than disulfide) in configuration/conformation.

The amino terminus of the peptide may be in the free amino form or may be acylated by a group of the formula RCO—, wherein R represents a hydrocarbyl group of 1–6C. The hydrocarbyl group is saturated or unsaturated and is typically, for example, methyl, ethyl, i-propyl, t-butyl, n-pentyl, cyclohexyl, cyclohexene-2-yl, hexene-3-yl, hexyne-4-yl, and the like.

The C-terminus of the peptides of the invention may be in the form of the underivatized carboxyl group, either as the free acid or an acceptable salt, such as the potassium, sodium, calcium, magnesium, or other salt of an inorganic ion or of an organic ion such as caffeine. The carboxyl terminus may also be derivatized by formation of an ester with an alcohol of the formula ROH, or may be amidated by an amine of the formula $NH_3$, or $RNH_2$, or $R_2NH$, wherein each R is independently hydrocarbyl of 1–6C as defined above. Amidated forms of the peptides wherein the C-terminus has the formula (SEQ ID NO: 1) $CONH_2$ are preferred.

As the peptides of the invention contain substantial numbers of basic amino acids, the peptides of the invention may be supplied in the form of the acid addition salts. Typical acid addition salts include those of inorganic ions such as chloride, bromide, iodide, fluoride or the like, sulfate, nitrate, or phosphate, or may be salts of organic anions such as acetate, formate, benzoate and the like. The acceptability of each of such salts is dependent on the intended use, as is commonly understood.

The amino acids in the peptides of the invention may be those encoded by the gene or analogs thereof, and may also be the D-isomers thereof. One preferred embodiment of the peptides of the invention is that form wherein all of the residues are in the D-configuration thus conferring resistance to protease activity while retaining antimicrobial or antiviral properties. The resulting clavanins are themselves enantiomers of the native L-amino acid-containing forms.

The amino acid notations used herein are conventional and are as follows:

| Amino Acid | One-Letter Symbol | Three-Letter Symbol |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The amino acids not encoded genetically are abbreviated as indicated in the discussion below.

In the specific peptides shown in the present application, the L-form of any amino acid residue having an optical isomer at the α carbon is intended unless the D-form is expressly indicated by a dagger superscript (†).

The compounds of the invention are peptides or peptide-like compounds which are partially defined in terms of amino acid residues of designated classes. Amino acid residues can be generally subclassified into major subclasses as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH.

Hydrophobic: The residues are not charged at physiological pH and the residue is repelled by aqueous solution so as to seek the inner positions in the conformation of a peptide in which it is contained when the peptide is in aqueous medium.

Neutral/polar: The residues are not charged at physiological pH, but the residue is not sufficiently repelled by aqueous solutions so that it would seek inner positions in the conformation of a peptide in which it is contained when the peptide is in aqueous medium.

This description also characterizes certain amino acids as "small" since their side chains are not sufficiently large, even if polar groups are lacking, to confer hydrophobicity. "Small" amino acids are those with four carbons or less when at least one polar group is on the side chain and three carbons or less when not.

It is understood, of course, that in a statistical collection of individual residue molecules some molecules will be charged, and some not, and there will be an attraction for or repulsion from an aqueous medium to a greater or lesser extent. To fit the definition of "charged," a significant percentage (at least approximately 25%) of the individual molecules are charged at the relevant pH. The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further subclassified as cyclic or noncyclic, and aromatic or nonaromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always nonaromatic.

For the naturally occurring protein amino acids, subclassification according to the foregoing scheme is as follows.

| | |
|---|---|
| Acidic | Aspartic acid and Glutamic acid |
| Basic | Noncyclic: Arginine, Lysine |
| | Cyclic: Histidine |
| Small | Glycine, Serine, Alanine, Threonine |
| Polar/large | Asparagine, Glutamine |
| Hydrophobic | Tyrosine, Valine, Isoleucine, Leucine, Methionine, Phenylalanine, Tryptophan |

The gene-encoded secondary amino acid proline is a special case due to its known effects on the secondary conformation of peptide chains, and is not, therefore, included in a group. Cysteine residues are also not included in these classifications since their capacity to form disulfide bonds to provide secondary structure may override the general polarity/nonpolarity of the residue. However, if a cysteine, which is, technically speaking, a small amino acid, is modified so as to prevent its participation in secondary structure, those locations indicated "S" in the compound of formula (1) may be inhabited by such modified cysteine residues. In addition, a single cysteine residue may occupy a position indicated by "S" although this is less favored because of the possibility of formation of intermolecular disulfides which may denature the antimicrobial activity of the compounds.

The "modified" amino acids that may be included in the clavanins are gene-encoded amino acids which have been processed after translation of the gene, e.g., by the addition of methyl groups or derivatization through covalent linkage to other substituents or oxidation or reduction or other covalent modification. The classification into which the resulting modified amino acid falls will be determined by the characteristics of the modified form. For example, if lysine were modified by acylating the ε-amino group, the modified form would not be classed as basic but as polar/large.

Certain commonly encountered amino acids, which are not encoded by the genetic code, include, for example, beta-alanine (beta-Ala), or other omega-amino acids, such as 3-aminopropionic, 2,3-diaminopropionic (2,3-diaP), 4-aminobutyric and so forth, alpha-aminisobutyric acid (Aib), sarcosine (Sar), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), 2-naphthylalanine (2-Nal); 1,2,3,4-tetrahydroisoquinoline-3-carboxylic acid (Tic); β-2-thienylalanine (Thi); methionine sulfoxide (MSO); and homoarginine (Har). These also fall conveniently into particular categories.

Based on the above definitions,

Sar, beta-Ala and Aib are small;

t-BuA, t-BuG, N-MeIle, Nle, Mvl, Cha, Phg, Nal, Thi and Tic are hydrophobic;

2,3-diaP, Orn and Har are basic;

Cit, Acetyl Lys and MSO are neutral/polar/large.

The various omega-amino acids are classified according to size as small (beta-Ala and 3-aminopropionic) or as large and hydrophobic (all others).

Other amino acid substitutions for those encoded in the gene can also be included in peptide compounds within the scope of the invention and can be classified within this general scheme according to their structure.

In all of the "peptides" of the invention, one or more amide linkages (—CO—NH—) may optionally be replaced with another linkage which is an isostere such as —CH$_2$NH—, —CH$_2$S—, —CH$_2$CH$_2$, —CH=CH— (cis and trans), —COCH$_2$—, —CH(OH)CH$_2$— and —CH$_2$SO—. This replacement can be made by methods known in the art. The following references describe preparation of peptide analogs which include these alternative-linking moieties: Spatola, A. F., *Vega Data* (March 1983), Vol. 1, Issue 3, "Peptide Backbone Modifications" (general review); Spatola, A. F., in "Chemistry and Biochemistry of Amino Acids Peptides and Proteins," B. Weinstein, eds., Marcel Dekker, New York, p. 267 (1983) (general review); Morley, J. S., *Trends Pharm Sci* (1980) pp. 463–468 (general review); Hudson, D., et al., *Int J Pept Prot Res* (1979) 14:177–185 (—CH$_2$NH—, —CH$_2$CH$_2$—); Spatola, A. F., et al., *Life Sci* (1986) 38:1243–1249 (—CH$_2$—S); Hann, M. M., *J Chem Soc Perkin Trans I* (1982) 307–314 (—CH=CH—, cis and trans); Almquist, R. G., et al., *J Med Chem* (1980) 23:1392–1398 (—COCH$_2$—); Jennings-White, C., et al., *Tetrahedron Lett* (1982) 23:2533 (—COCH$_2$—); Szelke, M., et al., European Application EP 45665 (1982) CA:97:39405 (1982) (—CH(OH)CH$_2$—); Holladay, M. W., et al., *Tetrahedron Lett* (1983) 24:4401–4404 (—C(OH)CH$_2$—); and Hruby, V. J., *Life Sci* (1982) 31:189–199 (—CH$_2$—S—)

The compounds of formula (1) are generally defined as set forth in the Disclosure of the Invention set forth above.

In preferred embodiments of the compounds of the invention,

X'$_1$ is Val, Leu, Ile, or Ala;

X$_2$ is Phe, Trp or Tyr;

B'$_3$ is Asn, Gln, His, Lys or Arg;

X$_4$ and X$_5$ is each independently selected from the group consisting of Phe, Leu, Tyr, and Val;

$S_6$ is Gly, Ser or Ala, preferably Gly;

$B_7$ is Lys or Arg;

$X_8$ and $X_9$ is each independently selected from the group consisting of Ile, Leu and Val;

$B_{10}$ and $B_{11}$ is each independently His, Lys or Arg, preferably His;

$X_{12}$ is Val, Ile, or Leu;

$U_{13}$ is Ala, Ser or Gly, preferably Gly;

$Z_{14}$ is Asn or Gln;

$X_{15}$ and $X_{16}$ is each independently selected from the group consisting of Phe, Tyr, Trp, Val, Leu and Ile, preferably $X_{15}$ is Phe and $X_{16}$ is Val, Ile or Leu;

$B^*_{17}$ is His, Lys, Arg, Trp, Phe or Tyr or a modified form thereof;

$U_{18}$ is Ala, Ser or Gly, preferably Gly;

$X_{19}$ is Phe, Tyr or Trp, preferably Phe;

$U_{20}$ is Gly, Ala or Ser, preferably Ser;

$B_{21}$ is His, Lys or Arg, preferably His; and each of $X_{22}$ and $X_{23}$ is Ile, Val, Leu, Phe, Tyr or Trp, most preferably $X_{22}$ is Val, Ile or Leu and $X_{23}$ is Phe, Tyr or Trp.

Also especially preferred are the C-terminal amidated forms of the compounds of the invention where the carboxyl terminus is of the formula —$CONH_2$.

Typical compounds within the scope of the clavanins are (SEQ ID NO: 10 through SEQ ID NO: 39):

| | | | | |
|---|---|---|---|---|
| VFNFL | GKIIH | HVGNF | VKGFS† | HVF* |
| IFQFL | GKIIH† | KVGNF | IHGFS | KVF* |
| VFHFL | GKIIH | HVGNF | VKGFS | HVF* |
| VFQFL | GKIIK | HVGNF | LHGFS | HVF |
| VFKFL | GKIVH | KVGNF | VKGFS | RVF* |
| LFQFL† | GKIIH† | HVGNF | IHGFS | HVY* |
| VFQFL | GKLIH | HVGNF | VHGFS | KVF* |
| IFQFL | GKIVH | KVGQF | LHGFS | KVF* |
| VFRFL | GKIVH | HVGNF | VRGFS | HVF* |
| SFQFL | GKIIK | HVGNF | LKGYS | RVF* |
| VFQFL | GK†ILH | HVGN†F | VHSFS | HLF |
| VFKFL | GKIIR | KVGNF | VHAFS† | KVF* |
| AFQFL | GKILK | RVGNF | LKGFS | HVY* |
| VFQFL | GKIIK | HVGN†F | VHGFS | RVF* |
| AFQFL | GKIIH | HVGNF | IKGFS | KVF* |
| VFKFL | GKVI†H | HVGQF | VHGFS | HVF* |
| VFQFL† | GKIIK | HVAQF | LHGFS | RVF* |
| VFHFL | GKIIH | HVGNF | VKGFS | HVW* |
| IFQ†FL | GKILK | LVGNF | VHGFG | HVF |
| VFQFL | GKIIH | KVGNY | VRGFS | KVF* |
| GFKFL | GKVIH | HVANW | LHGFS | KVF* |
| LFQFL | GKIIK | HVSNF | VKGFS | HVF* |
| VFRFL | GKIIK | KVGNF | VHGFA | KVF* |
| SFQFL | GKIIR | KVGQF | IHGFG | HVF* |
| VFQFL | GKIVH | KVANF | LHGFS | HVW* |
| VFNFL | GKIIR | RVGNF | VKGFS | RVF* |
| AFKFL | GKLIH | HVGNF† | IHGFG | HVY* |
| VFQFL | GKIIR | KVGNF | VKGFS | KVY* |
| VFNFL | GK†IIH | KVGNF | VHGFS | KVF* |
| AFQFL | GKIVH | H†VGNF | LHGFA | HVW* |

Also preferred are compounds with the consensus sequence (SEQ ID NO: 40):

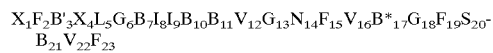

wherein $X_1$, $B'_3$, $X_4$, $B_7$, $B_{10}$, $B_{11}$, $B^*_{17}$, and $B_{21}$ are as defined above.

Preferred among these are embodiments wherein:

$X_1$ is Ala, Leu or Val; or $B'_3$ is Gln, His or Lys; or $X_4$ is Leu or Phe; or $B_7$ is Arg or Lys; or $B_{10}$, $B_{11}$ and $B_{21}$ are His or Lys; or $B^*_{17}$ is His, Lys or modified Tyr, especially those wherein:

$X_1$ is Ala or Val; and $B'_3$ is Gln, His or Lys; and $X_4$ is Leu or Phe; and $B_7$ is Arg or Lys; and $B_{10}$, $B_{11}$ and $B_2$l are His or Lys; and $B^*_{17}$ is His, Lys or modified Tyr.

Particularly preferred forms of the compounds of the invention are Clavanins A, B C and D, shown below in comparison with Magainin 1 and Magainin 2.

| | | | | | |
|---|---|---|---|---|---|
| Magainin 1 (SEQ ID NO: 41) | —GI | GKFLH | SAGKF | GKAFV | GEI MKS |
| Magainin 2 (SEQ ID NO: 42) | —GI | GKFLK | SAGKF | GKAFV | NEI MKS |
| Clavanin A (SEQ ID NO: 43) | VFQFL | GKIIH | HVGNF | VHGFS | HVF* |
| Clavanin B (SEQ ID NO: 44) | VFQFL | GRIIH | HVGNF | VHGFS | HVF* |
| Clavanin C (SEQ ID NO: 45) | VFHLL | GKIIH | HVGNF | VY'GFS | HVF* |
| Clavanin D (SEQ ID NO: 46) | AFKLL | GRIIH | HVGNF | VY'GFS | HVF* |
| Clavanin E (SEQ ID NO: 47) | LFKLL | GKIIH | HVGNF | VHGFS | HVF |

*indicates the amide form.

Preparation of the Invention Compounds

The invention compounds, often designated herein "clavanins" are essentially peptide backbones which may be modified at the N-or C-terminus and are linear peptides.

Standard methods of synthesis of peptides the size of clavanins are known. Most commonly used currently are solid phase synthesis techniques; indeed, automated equipment for systematically constructing peptide chains can be purchased. Solution phase synthesis can also be used but is considerably less convenient. When synthesized using these standard techniques, amino acids not encoded by the gene and D-enantiomers can be employed in the synthesis. Thus, one very practical way to obtain the compounds of the invention is to employ these standard chemical synthesis techniques.

In addition to providing the peptide backbone, the N- and/or C-terminus can be derivatized, again using conventional chemical techniques. The compounds of the invention may optionally contain an acyl group, preferably an acetyl group at the amino terminus. Methods for acetylating or, more generally, acylating, the free amino group at the N-terminus are generally known in the art; in addition, the N-terminal amino acid may be supplied in the synthesis in acylated form.

At the carboxy terminus, the carboxyl group may, of course, be present in the form of a salt; in the case of pharmaceutical compositions this will be a pharmaceutically acceptable salt. Suitable salts include those formed with inorganic ions such as $NH_4^+$, $Na^+$, $K^+$, $Mg^{++}$, $Ca^{++}$, and the like as well as salts formed with organic cations such as those of caffeine and other highly substituted amines. The carboxy terminus may also be esterified using alcohols of the formula ROH wherein R is hydrocarbyl (1–6C) as defined above. Similarly, the carboxy terminus may be amidated so as to have the formula —$CONH_2$, —CONHR, or —$CONR_2$, wherein each R is independently hydrocarbyl (1–6C) as herein defined. Techniques for esterification and amidation as well as neutralizing in the presence of base to form salts are all standard organic chemical techniques.

If the peptides of the invention are prepared under physiological conditions, the side-chain amino groups of the basic amino acids will be in the form of the relevant acid addition salts.

If the peptide backbone is comprised entirely of gene-encoded amino acids, or if some portion of it is so composed, the peptide or the relevant portion may also be synthesized using recombinant DNA techniques. The DNA encoding the peptides of the invention may itself be synthesized using commercially available equipment; codon choice can be integrated into the synthesis depending on the nature of the host.

Recombinantly produced forms of the clavanins may require subsequent derivatization to modify the N- and/or C-terminus.

For recombinant production, the DNA encoding the clavanins of the invention is included in an expression system which places these coding sequences under control of a suitable promoter and other control sequences compatible with an intended host cell. Types of host cells available span almost the entire range of the plant and animal kingdoms. Thus, the clavanins of the invention could be produced in bacteria or yeast (to the extent that they can be produced in a nontoxic or refractile form or utilize resistant strains) as well as in animal cells, insect cells and plant cells. Indeed, modified plant cells can be used to regenerate plants containing the relevant expression systems so that the resulting transgenic plant is capable of self protection vis-à-vis these infective agents.

The clavanins of the invention can be produced in a form that will result in their secretion from the host cell by fusing to the DNA encoding the clavanin, a DNA encoding a suitable signal peptide, or may be produced intracellularly. They may also be produced as fusion proteins with additional amino acid sequence which may or may not need to be subsequently removed prior to the use of these compounds as antimicrobials.

Thus, the clavanins of the invention can be produced in a variety of modalities including chemical synthesis and recombinant production or some combination of these techniques.

Any members of the clavanin class which occur naturally are supplied in purified and isolated form. By "purified and isolated" is meant free from the environment in which the peptide normally occurs (in the case of such naturally occurring peptides) and in a form where it can be used practically. Thus, "purified and isolated" form means that the peptide is substantially pure, i.e., more than 90% pure, preferably more than 95% pure and more preferably more than 99% pure or is in a completely different context such as that of a pharmaceutical preparation.

Antibodies

Antibodies to the clavanins of the invention may also be produced using standard immunological techniques for production of polyclonal antisera and, if desired, immortalizing the antibody-producing cells of the immunized host for sources of monoclonal antibody production. Techniques for producing antibodies to any substance of interest are well known. It may be necessary to enhance the immunogenicity of the substance, particularly as here, where the material is only a short peptide, by coupling the hapten to a carrier. Suitable carriers for this purpose include substances which do not themselves produce an immune response in the mammal to be administered the hapten-carrier conjugate. Common carriers used include keyhole limpet hemocyanin (KLH), diphtheria toxoid, serum albumin, and the viral coat protein of rotavirus, VP6. Coupling of the hapten to the carrier is effected by standard techniques such as contacting the carrier with the peptide in the presence of a dehydrating agent such as dicyclohexylcarbodiimide or through the use of linkers such as those available through Pierce Chemical Company, Chicago, Ill.

The clavanins of the invention in immunogenic form are then injected into a suitable mammalian host and antibody titers in the serum are monitored.

Polyclonal antisera may be harvested when titers are sufficiently high. Alternatively, antibody-producing cells of the host such as spleen cells or peripheral blood lymphocytes may be harvested and immortalized. The immortalized cells are then cloned as individual colonies and screened for the production of the desired monoclonal antibodies. The genes encoding monoclonal antibodies secreted by selected hybridomas or other cells may be recovered, manipulated if desired, for example, to provide multiple epitope specificity or to encode a single-chain form and may be engineered for expression in alternative host cells, such as CHO cells.

Thus, as used herein, "antibodies" also includes any immunologically reactive fragment of the immunoglobulins such as Fab, Fab' and F(ab') fragments as well as modified immunoreactive forms such as Fv regions, which are produced by manipulation of the relevant genes (isolable, for example, from the appropriate hybridoma).

The antibodies of the invention are, of course, useful in immunoassays for determining the amount or presence of the clavanins. Such assays are essential in quality controlled production of compositions containing the clavanins of the invention. In addition, the antibodies can be used to assess the efficacy of recombinant production of the clavanins, as well as for screening expression libraries for the presence of clavanin encoding genes. They may also be used as affinity ligands for purifying and/or isolating the clavanins.

Compositions Containing the Clavanins and Methods of Use

The clavanins of the invention are effective in inactivating a wide range of microbial, including viral targets, including gram-positive and gram-negative bacteria, yeast, protozoa and certain strains of virus. Accordingly, they can be used in disinfectant compositions and as preservatives for materials such as foodstuffs, cosmetics, medicaments, or other materials containing nutrients for organisms. For use in such contexts, the clavanins are supplied either as a single clavanin, in admixture with several other clavanins, or in admixture with additional antimicrobial agents. In general, as these are preservatives in this context, they are usually present in relatively low amounts, of less than 5%, by weight of the total composition, more preferably less than 1%, still more preferably less than 0.1%.

The peptides of the invention are also useful as standards in antimicrobial assays and in assays for determination of capability of test compounds to bind to endotoxins such as lipopolysaccharides.

For use as antimicrobials or antivirals for treatment of animal subjects, the clavanins of the invention can be formulated as pharmaceutical or veterinary compositions. Depending on the subject to be treated, the mode of administration, and the type of treatment desired—e.g., prevention, prophylaxis, therapy; the clavanins are formulated in ways consonant with these parameters. A summary of such techniques is found in Remington's *Pharmaceutical Sciences,* latest edition, Mack Publishing Co., Easton, Pa.

In general, for use in treatment or prophylaxis, the clavanins of the invention may be used alone or in combination with other antibiotics such as erythromycin, tetracycline, macrolides, for example azithromycin and the cephalosporins. Depending on the mode of administration, the clavanins will be formulated into suitable compositions to permit facile delivery to the affected areas. Use of the enantiomeric forms containing all D-amino acids may confer advantages such as resistance to those proteases, such as trypsin and chymotrypsin, to which the clavanins containing L-amino acids are less resistant.

The clavanins of the invention can be administered singly or as mixtures of several clavanins or in combination with other pharmaceutically active components, and in single or multiple administrations. The formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The clavanins can be administered also in liposomal compositions or as microemulsions.

If administration is to be oral, the clavanins of the invention must be protected from degradation in the stomach using a suitable enteric coating. This may be avoided to some extent by utilizing amino acids in the D-configuration, thus providing resistance to protease. However, the peptide is still susceptible to hydrolysis due to the acidic conditions of the stomach; thus, some degree of enteric coating may still be required.

As the examples will show, by appropriately choosing the member of the clavanin class of the invention, it is possible to adapt the antimicrobial activity to maximize its effectiveness with respect to a particular target microbe. As used herein, "microbe" will be used to include not only yeast, bacteria, and other unicellular organisms, but also viruses. The particular clavanin can also be chosen to be advantageous in a particular context, such as low salt or physiological salt, the presence or human serum, or conditions that mimic the conditions found in blood and tissue fluids.

Since certain forms of the clavanins are enhanced in effectiveness at reduced pH (i.e., those wherein histidine represents several of the basic residues, these forms can advantageously be used in low pH environments such as the stomach or sites of inflammation.

The clavanins of the invention may also be applied to plants or to their environment to prevent microbial-induced including viral diseases in these plants. Suitable compositions for this use will typically contain a diluent as well as a spreading agent or other ancillary agreements beneficial to the plant or to the environment.

Thus, the clavanins of the invention may be used in any context wherein an antimicrobial action is required. This use may be an entirely in vitro use, or the peptides may be administered to organisms.

In addition, the antimicrobial, including antiviral activity may be generated in situ by administering an expression system suitable for the production of the clavanins of the invention. Such expression systems can be supplied to plant and animal subjects using known techniques. For example, in animals, pox-based expression vectors can be used to generate the peptides in situ. Similarly, plant cells can be transformed with expression vectors and then regenerated into whole plants which are capable of their own production of the peptides.

The following examples are intended to illustrate but not to limit the invention.

EXAMPLE 1

Preparation of Clavanins A-D from *S. clava*

Tunics of *Styela clava* in batches of 50, obtained from Marinus Biologicals, Long Beach, Calif. were bathed briefly in absolute ethanol, blotted dry and transected peribasally over a 50 ml test tube that contained 0.25 g of disodium EDTA, into which the hemolymph was collected dripwise, and filtered through a fine sieve to remove components larger than hemocytes. $2 \times 10^8$ hemocytes were obtained and centrifuged (260× g, 5 min, 4° C.), resuspended in 50 ml of 0.34 M sucrose, recentrifuged and then extracted into ice cold 5% acetic acid, aided by brief sonication and overnight stirring at 4° C. The extract was centrifuged at 27,000× g for 30 min and the supernatants, which contained approximately 15 mg protein by BCA analysis, were removed for subsequent purification by the steps of ultrafiltration through a 10 kDa cutoff Amicon YM-10 membrane, followed by either gel permeation chromatography or (more usually) preparative electrophoresis, followed by reversed phase HPLC.

In more detail, the filtrates (≈3.5 mg of protein by BCA) were concentrated to 2 ml by vacuum centrifugation in a Speed Vac Concentrator (Savant Instruments, Hicksville, N.Y.). Gel permeation chromatography was performed on a 1.2×65 cm BioGel P-10 gel permeation column with 5% acetic acid. Preparative continuous acid-urea PAGE electrophoresis was performed as described by Harwig, S. S. L. et al., *Anal Biochem* (1993) 208:382. Active fractions were pooled and purified by RP-HPLC a 4.6×250 mm Vydac C18 column, using various linear gradients of acetonitrile in 0.1% trifluoroacetic acid (TFA) or 0.13,) heptafluorobutyric acid (HFBA). Throughout this multistep procedure, fractions were lyophilized, concentrated and tested for antimicrobial activity against *Listeria monocytogenes* strain EGD by a radial diffusion technique described in Lehrer, R. I. et al., *J Immunol Methods* (1991) 137:167. In these assays, the underlay gels contained 9 mM sodium phosphate and 1 mM sodium citrate buffer, 0.30 mg/ml of trypticase soy broth powder (BBL, Cockeysville, Md.) and 10 agarose at a final pH of 6.5.

Figure 1B:
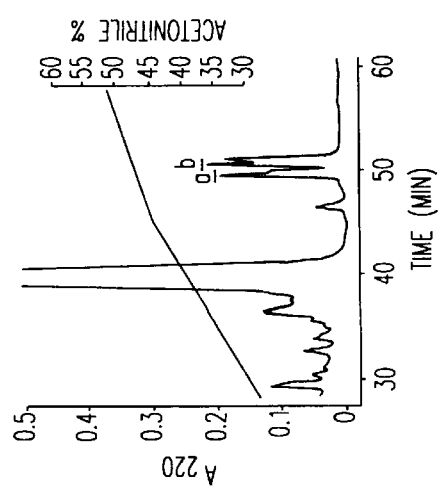
Figure 1C:
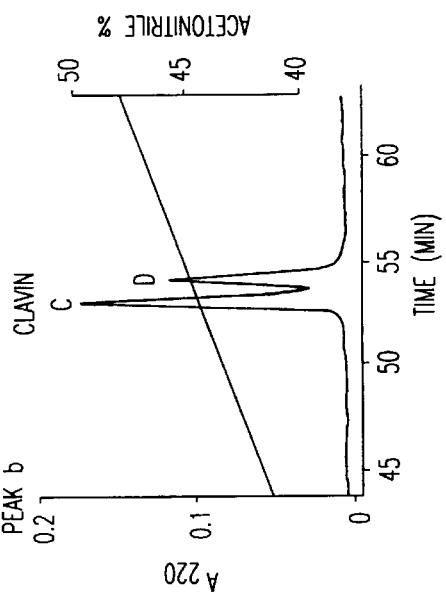

FIG. 1 shows the results of final purification on HPLC. As shown in FIG. 1, initial separation provided peaks a and b which were then rechromatographed to separate peak a into Clavanins A and B and peak b into Clavanins C and D. Neither Clavanin A nor Clavanin B showed significant absorbency at 280 nm although Clavanins C and D both showed such absorbency.

Amino acid compositions were determined for Clavanins A and B; the hydrolysis of Clavanins C and D showed an unknown peak that emerged before phenylthiocarbamyl (PTC) tyrosine, suggesting the presence of one or more modified or unusual amino acid residues, although the retention time of this peak did not match either PTC-methyl lysine or PTC-methyl histidine.

As shown below, the complete amino acid sequences of Clavanins A–D were determined in part by gas-phase Edman degradation with a Portion Model 2090 instrument using 300 pmole samples. Y' indicates a modified tyrosine residue, in this case, o-methyl tyrosine. The * indicates amidation.

| Clavanin A (SEQ ID NO: 43) | VFQFL | GKIIH | HVGNF | VHGFS | HVF* |
|---|---|---|---|---|---|
| Clavanin B (SEQ ID NO: 44) | VFQFL | GRIIH | HVGNF | VHGFS | HVF* |

| | | | | | |
|---|---|---|---|---|---|
| Clavanin C (SEQ ID NO: 45) | VFHLL | GKIIH | HVGNF | VY'GFS | HVF* |
| Clavanin D (SEQ ID NO: 46) | AFKLL | GRIIH | HVGNF | VY'GFS | HVF* |

Nineteen of the 22 residues of Clavanins C and D could be identified by direct peptide sequencing as indicated above. The remaining residues, $Tyr_{17}$, $His_{21}$, $Val_{22}$ and $Phe_{23}$ were identified by 3' RACE-PCR cloning of a precursor having the partial sequence HHVGNFV YGFSHVF(G)(SEQ ID NO: 48). The masses for Clavanins C and D as determined by FAB-MS were 14 mass units less than their measured values, suggesting that one residue was methylated. Because no unmodified tyrosine was found in the amino acid analysis, the methylated residue appears to be $Tyr_{17}$. The presence and position of the parenthesized glycine residue in the precursor suggests that Clavanins C and D are amidated. This is consistent with the amidation of Clavanins A and B set forth below.

Two forms of synthetic Clavanin A were prepared, one as the free acid at the C-terminus and the other in C-terminal amidated form. These were synthesized by SynPep, Dublin, Calif., using F-moc chemistry. The electrospray $mass_{av}$ values for the acid form were 2667.2 (expected 2667.1) and for the amide 2664.6 (expected 2666.1) and the peptides were purified to apparent homogeneity by reverse-phase HPLC. By comparing migration values by AU PAGE, it was concluded that both Clavanin A and Clavanin B contained C-terminal amidation.

Mass values for the clavanins are as follows:

Clavanin A: 2667.1;

Clavanin B: 2694.8;

Clavanin C: 2682.1;

Clavanin D: 2673.0.

EXAMPLE 2

Characterization of Conformation

Figure 2A:
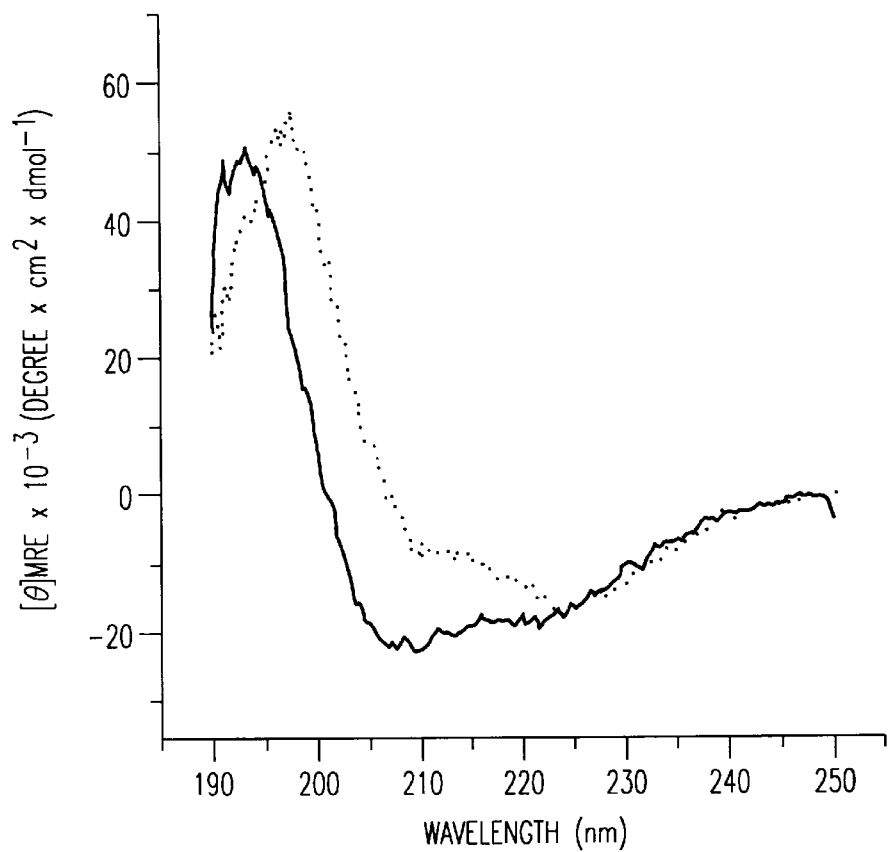
FIG. 2 shows the circular dichroism pattern for Clavanin A and a helical wheel projection of the structure based on these results.
Figure 2B:
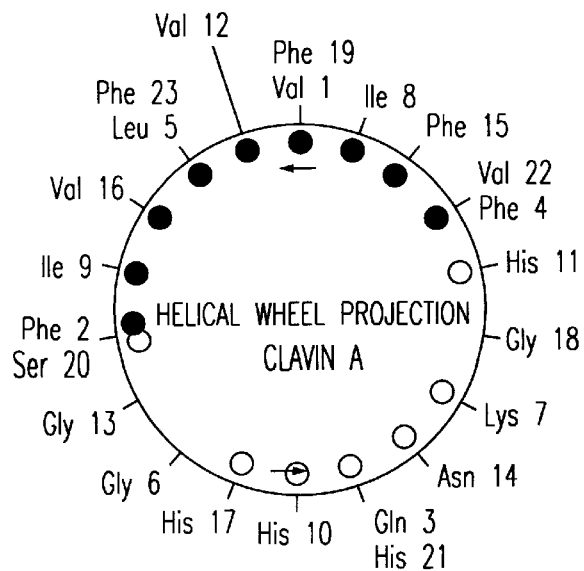

The circular dichroism spectrum for synthetic Clavanin A was determined on an Aviv Model 62DS Spectral Polarimeter (Aviv Associates, Lakewood, N.J.) in 80% TFA at 25° C. using a rectangular cell with a 0.5 mm path length. Similar measurements were made using synthetic Clavanin A contained in large (≈100 nm) unilamellar liposomes of simulated S. aureus lipids contained in a 3:1 molar ratio of egg phosphatidyl glycerol and cardiolipin, prepared by an extrusion technique using a LiposoFast device (Avestin, Ottawa, Canada). The results are shown in FIG. 2 for the synthetic form and show a characteristic α-helical conformation with a double minimum at ≈208 and ≈222 nm. Similarly determined spectra of native Clavanin A displayed maxima at ≈210 and ≈224 nm. FIG. 2 also shows a helical wheel projection of Clavanin A indicating an amphipathic helix with spatial segregation of the hydrophobic and charged residues.

EXAMPLE 3

Recovery of Clavanin-Encoding cDNA

Total RNA from tunicate pharyngeal tissues was isolated and purified using a total RNA separator kit (Clontech, Palo Alto, Calif.). First strand cDNA synthesis and clavanin 3' side cDNA amplification were carried out with a 3'RACE kit (Gibco BRL, Gaithersburg, Md.) using 1 μg of total pharyngeal RNA, and 10 μM adapter primer to obtain the first strand of cDNA. A degenerate 30-base primer, 5'-GTCGACTAGTCAYCAYGTIGGIAAYTTYGT-3'(SEQ ID NO: 49), where $\underline{\underline{Y}}$ represents T or C, $\underline{\underline{I}}$ represents inosine, and the single underlining indicates a Spe I restriction site that corresponded to amino acids 11–17 of clavanins A, B, C, and D (His-His-Val-Gly-Asn-Phe-Val(SEQ ID NO: 50) was designed.

PCR was performed in a total volume of 50 μl that contained: 1/10 vol. of first strand cDNA, 10 pmol each of degenerate primer and AUAP primer, and 5 U of pfu DNA polymerase. The reaction was run for 35 cycles, with 1 min denaturation (94° C.), 1 min annealing (48° C.), and 2.5 min extension (72° C.) per cycle. PCR product about 250 bp in size was cloned into pCRScript SK vector (Stratagene, La Jolla, Calif.). DNA sequencing results confirmed that it was the 3' side cDNA sequence of clavanin.

To obtain a DNA library, pharyngeal tissues (the functional equivalent of bone marrow in tunicates) were removed from live Styela clava and stored at -70° C. A custom cDNA library was constructed for us in λTripIEx™ by Clontech Laboratories. E. coli stain XL1-Blue was used as a host, and phage plaques DNA was transferred to nylon membranes (Dupont, Boston, Mass.). The filters were hybridized with $^{32}$P-labeled 250 bp clavanin 3' side cDNA, as per the above. Hybridization was carried out at 50° C. overnight with Rapid-hyb buffer (Amersham). The filters were washed several times, finally at 60° C. in 0.1×SSC and 0.1% SDS, and exposed to S-ray film with an intensifying screen at -70° C. Positive clones were subjected to one or two additional rounds of plaque screening at low density. Finally, 50 positive clones were identified from approximately $1.2 \times 10^5$ clones.

To obtain DNA sequence, λ phage DNA was purified using a Lamda kit (AIAGEN, Chatsworth, Calif.). The purified DNA or picked plaques were subjected to long-distance PCR using LD-Insert Screening Amplimers (Clontech Lab., Palo Alto, Calif.). PCR amplification was performed according to the manufacturer's protocol. The PCR products of inserts were purified from low melting agarose gel, and sequenced directly by fluorescein-labeled dideoxynucleotide terminator method, and the sequencing reaction were analyzed on an Applied Biosystems 373 DNA Sequencer (Perkin-Elmer, Palo Alto, Calif.). Of the eight clones sequenced to date, we have found 2 clavanin A, 4 clavanin D, 1 clavanin D, and 1 clavanin E. The sequence of each precursor is shown in FIGS. 3A–3E.

The 5'-cDNA inserts contain a short untranslated part (≈20 bp). As shown from the sequence information, clavanins are synthesized as prepropeptides with a typical, ~18–20 residue-long signal sequence followed by a short anionic propiece (SL)(EERKSEEEK)(SEQ ID NO: 51). A glycine residue follows the amino acids present in the mature clavanins, as expected for amidated peptides. Finally, there are 27 amino acids that follow the mature clavanin + glycine sequence. (See FIG. 3E)

Thus, the clavanins are encoded as C-terminal extended proclavanins; post-translational processing removes the C-terminal 27 amino acids and amidates the residual peptide chain.

EXAMPLE 4

Antimicrobial Activity of the Clavanins

In initial experiments, the antimicrobial activity of Clavanin A was compared with that of the known antimicrobial peptides Magainin 1 and Cecropin P1 against *Listeria monocytogenes* and *E. coli* by a classical colony counting technique. The peptides were mixed with midlogarithmic phase bacteria in a sterile solution of 10 mM sodium phosphate buffer, pH 6.5 containing 0.3 mg/ml of trypticase soy broth powder. Approximately 50–100 µl of the mixtures were incubated in a 37° C. shaking water bath and 10 µl aliquots removed at intervals and either plated directly or diluted with a Spiral Plater (Spiral Systems Instruments, Bethesda, Md.) as described by Gilchrist, J. E. et al., *J Assoc Off Anal Chem* (1977) 60:807. The colonies were counted after overnight incubation.

Figure 4:
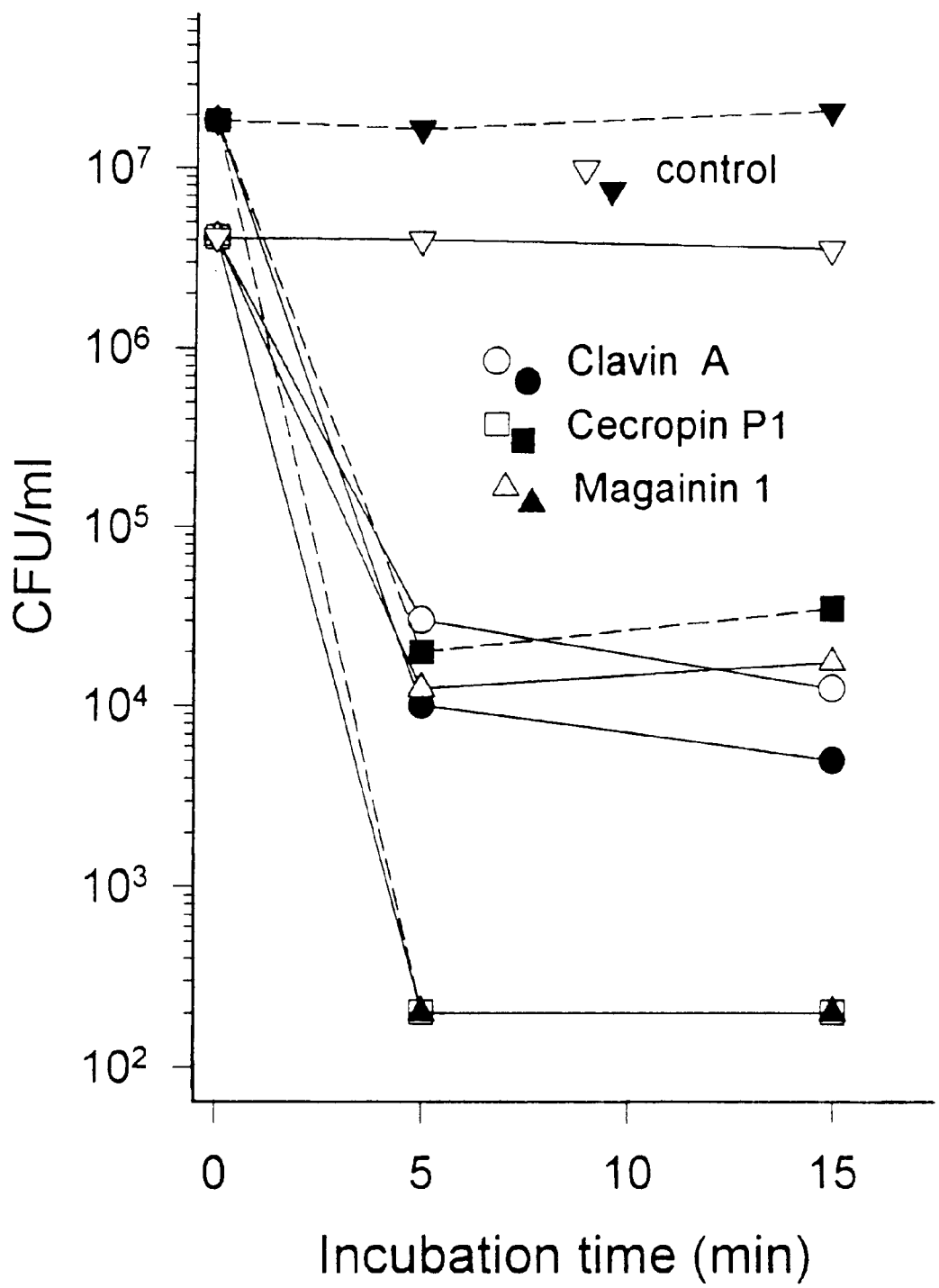
FIG. 4 shows a graphic representation of antimicrobial activity of Clavanin A against E. coli and L. monocytogenes as compared to the activity of Cecropin P1 and Magainin 1.

The results are shown in FIG. 4.

All of the peptides, provided at low concentrations, killed these bacteria within 5 min. Clavanin A and Magainin 1 at 1.6 µg/ml showed identical activity against *E. coli* ML-35P, reducing the colony count by more than 2 log units; at 3.5 µg/ml Clavanin A caused a rapid more-than-3 log unit reduction in *L. monocytogenes* CFU, an effect that was intermediate between that of Cecropin P1 and that of Magainin 1.

Figures 5A, 5B, 5C:
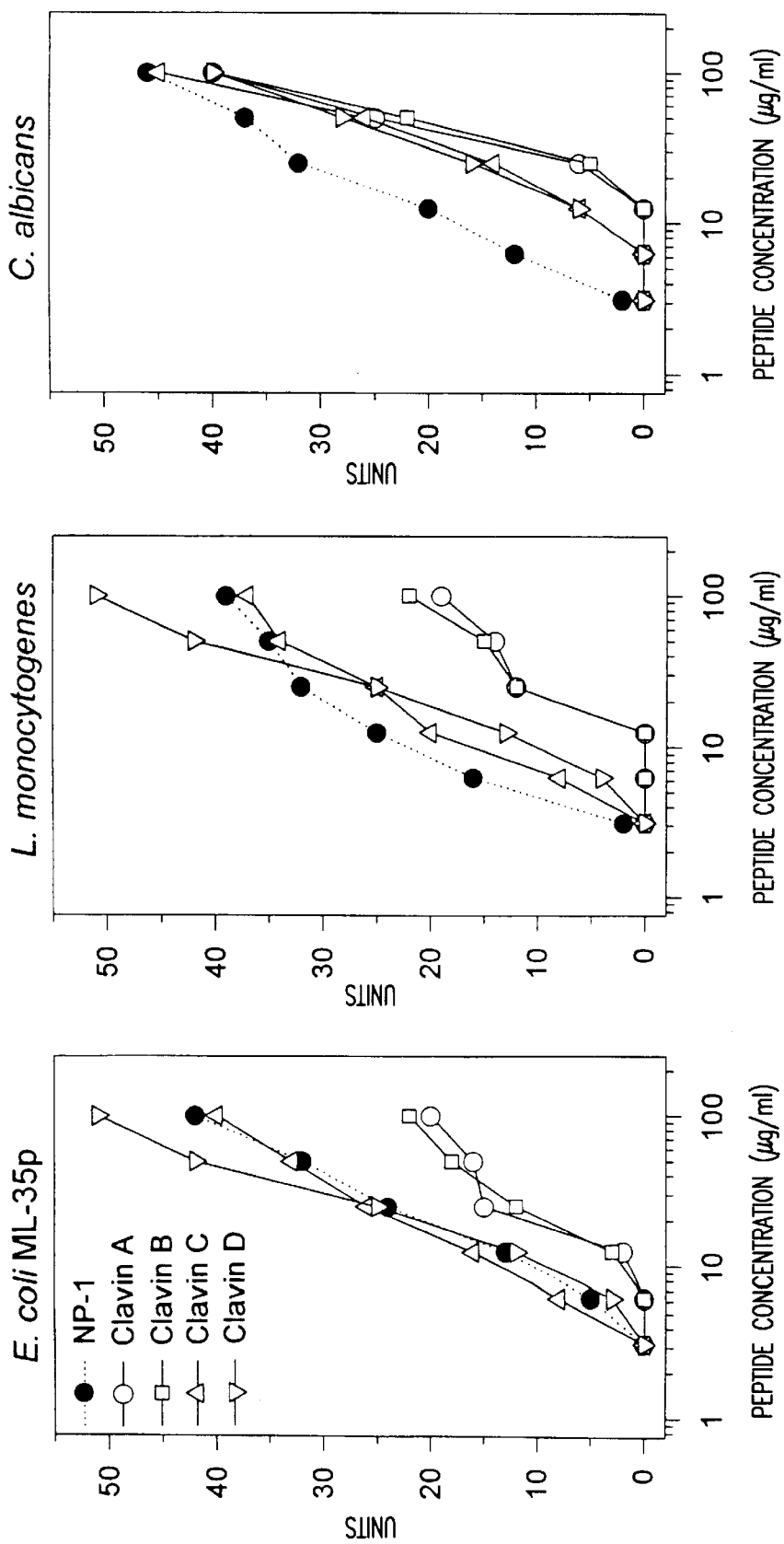
FIG. 5 shows comparative antimicrobial activity of Clavanins A, B, C and D with respect to E. coli, L. monocytogenes and C. albicans.
Figure 6A:
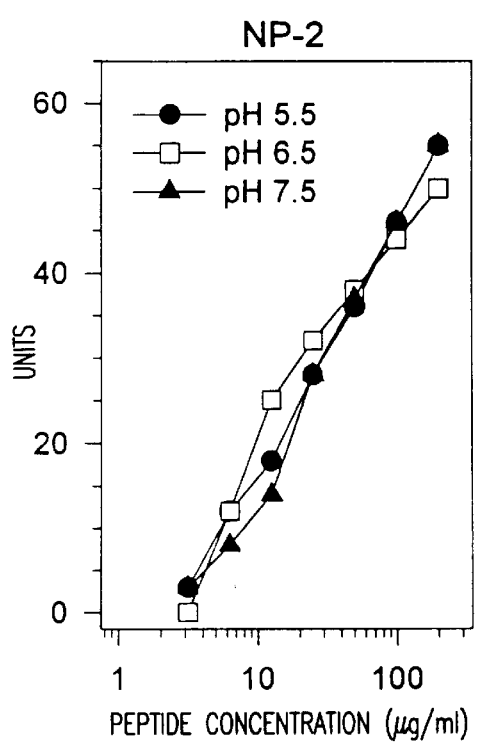
FIG. 6 shows antimicrobial activity, against L. monocytogenes, of native Clavanin A, synthetic Clavanin A and a modified form of Clavanin A wherein the histidine residues are replaced by lysine (Clavanin A(K)) as a function of pH.
Figure 6B:
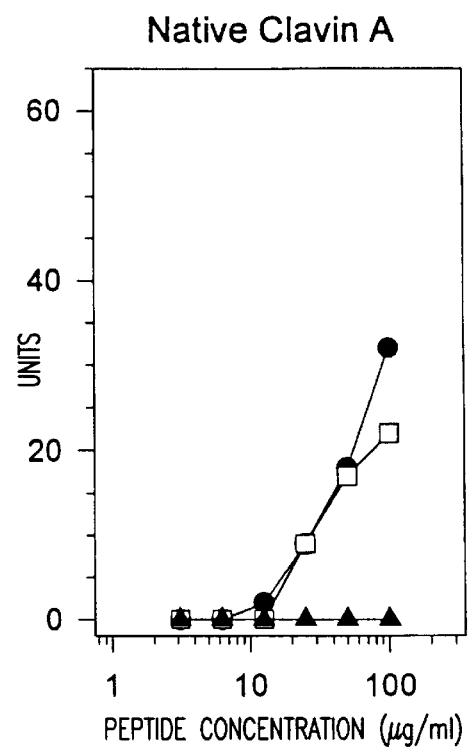
Figure 6C:
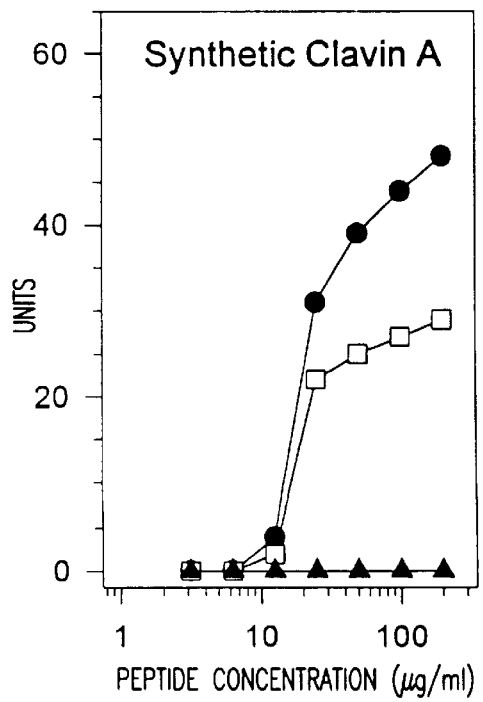
Figure 6D:
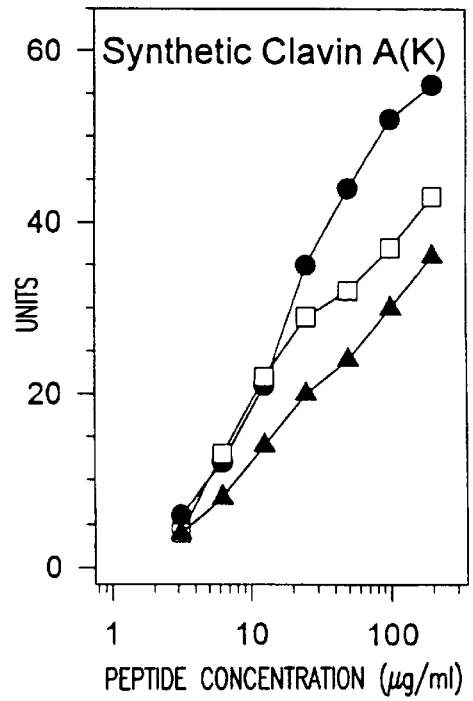
Figure 7A:
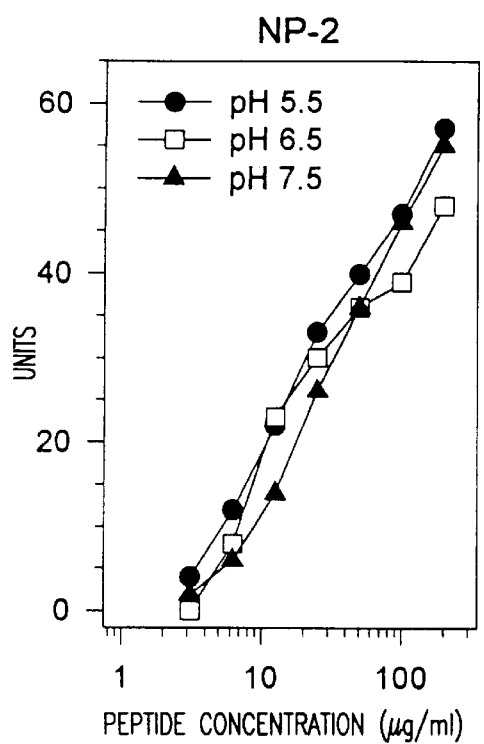
FIG. 7 shows a similar comparison to that of FIG. 6 with respect to E. coli.
Figure 7B:
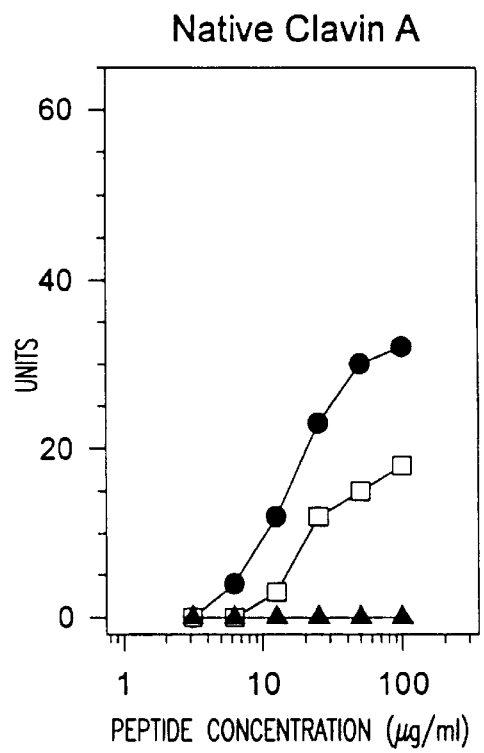
Figure 7C:
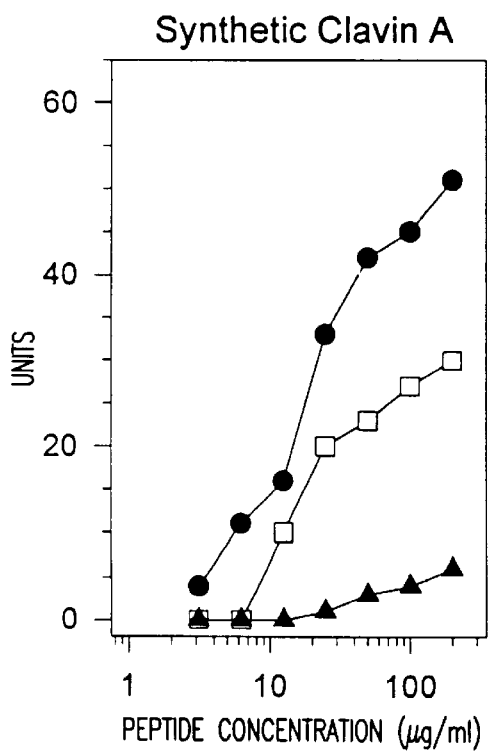
Figure 7D:
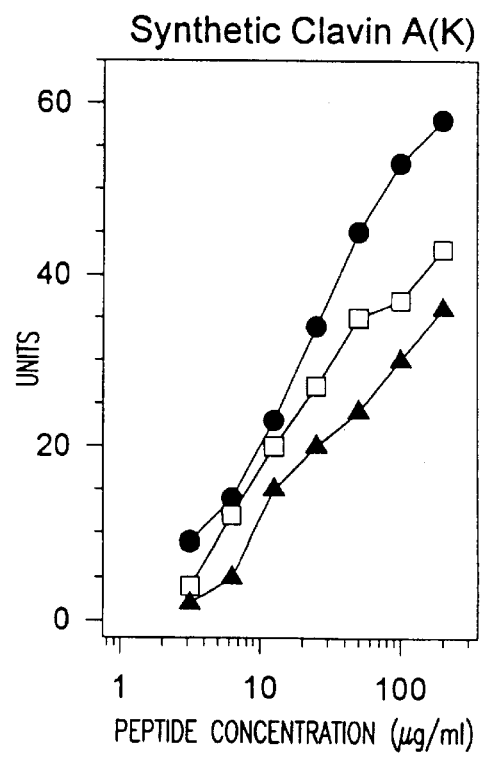

FIG. 5 shows the results of antimicrobial assays conducted using a more sensitive radial diffusion method of Lehrer et al. (supra) against *E. coil* ML-35P, *L. monocytogenes* Strain EGD and yeast phase *C. albicans*. Clavanins C and D were approximately 3–5-fold more potent than A and B with respect to the bacterial assays although similar results were obtained against *C. albicans*.

In addition to Cecropin P1 and Magainin 1, the activity of Clavanin A(K) was also tested. Clavanin A(K) is identical to Clavanin A except that all of the histidine residues are replaced by lysine. Table 1 shows a summary of the comparative activities of the peptide Cecropin P1, Magainin 1, Clavanin A and Clavanin A(K) versus a number of Gram-positive and Gram-negative bacteria. The data are provided as minimal bacteriocidal concentrations expressed in µg/ml which are the X-intercepts of radial diffusion assays performed at pH 6.5 in an underlay that contained 10 mM buffer (9:1 citrate:phosphate), 1% agarose and 0.3 mg trypticase soy powder/ml.

EXAMPLE 5

Effect of pH on Antimicrobial Activity

Figure 8C:
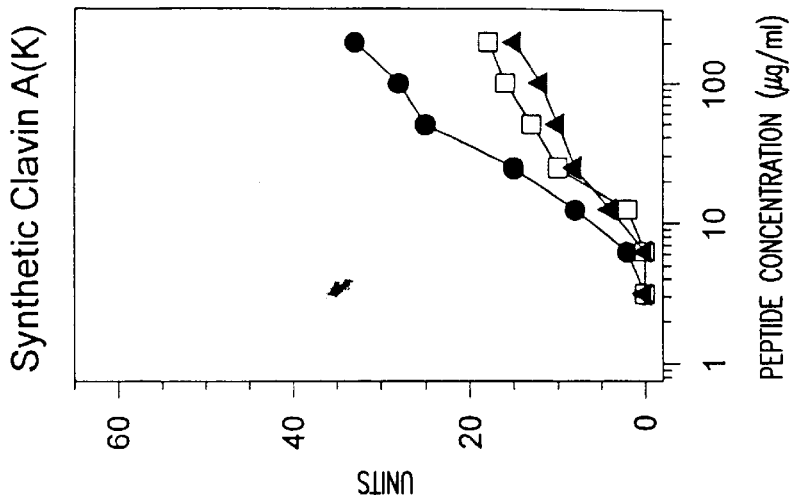
FIG. 8 shows a similar comparison to that of FIG. 6 with respect to C. albicans.
Figure 8B:
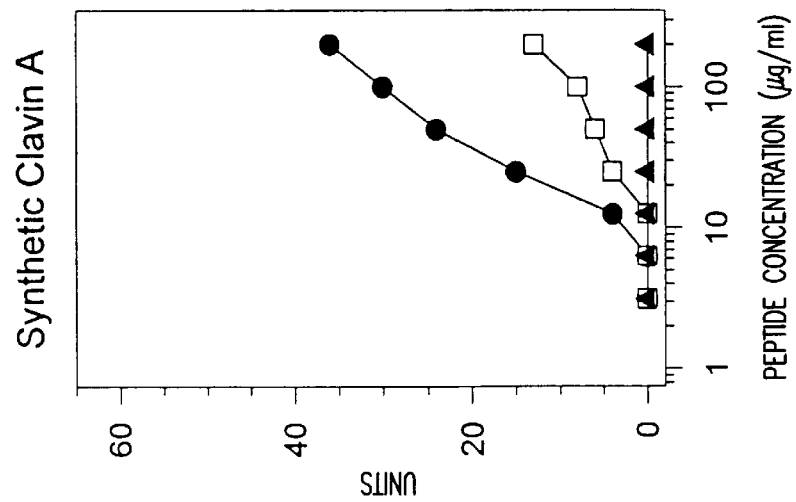
Figure 8A:
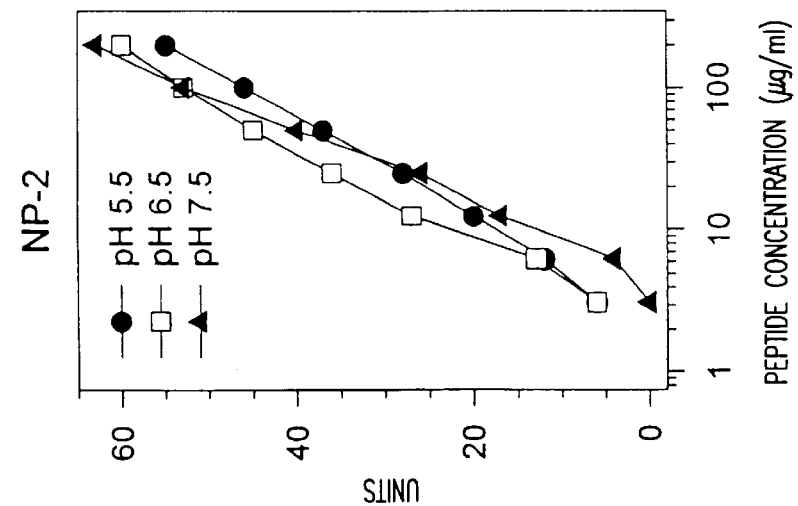

The effect of pH on antimicrobial activity against several organisms was tested in a pH range wherein histidine becomes comparably charged to lysine. FIGS. 6–8 show the results for native or synthetic Clavanin A and synthetic Clavanin A(K) using defensin NP-2 as a control, with respect to *L. monocytogenes*, *E. coli*, and *C. albicans* respectively. The radial diffusion assays were conducted as described in Examples 1 and 3 above. As shown in FIG. 6, the pH of the assay has no effect on the activity of defensin NP-2, but both native Clavanin A and synthetic Clavanin A are relatively inactive at pH 7.5 although they are highly antimicrobial at pH 5.5–6.5. Synthetic Clavanin A(K) is comparably active at all three pHs. Similar results are obtained as shown in FIGS. 7 and 8 for *E. coli* and *C. albicans*.

EXAMPLE 6

Effect of Other Parameters

A comparison of the antimicrobial activity of synthetic Clavanin A in the amide and free-acid form against *L. monocytogenes* and *E. coli* showed that both behaved similarly with respect to both bacteria.

When the radial diffusion assays were run adding 100 mM NaCl to the underlay gels, the presence of the salt appeared to diminish but not to destroy the activity of the synthetic Clavanin A peptide with respect to *L. monocytogenes* and *E. coli*.

The kinetics of the antimicrobial activity of Clavanin A and Clavanin A(K) were also tested in a colony count assay using 10 mM sodium phosphate plus 1:100 TSB buffer at pH 6.5. Mid log phase *L. monocytogenes* were incubated with 3.5 or 7.0 µg/ml of the test peptides and samples were removed after 5 and 15 min; concentrations with respect to

| Organism: | Cecropin P1 | Magainin 1 | Clavanin A | Clavanin A(K) |
|---|---|---|---|---|
| Gram-positive | | | | |
| *S. aureus* 930918-3 | >200 | >200 | >200 | 6.8 |
| MRSA 30371 | >200 | >200 | 6.7 | 5.6 |
| MRSA 28841 | >200 | >200 | 1.4 | 2.5 |
| *E. faecalis* CDC 21 (VR) | >200 | >200 | 1.7 | 6.5 |
| *E. faecium* 94.132 (VR) | 7.5 | 5.5 | 0.14 | 0.36 |
| *E. faecium* | 6.5 | 7.3 | 0.77* | 0.67 |
| *L. monocytogenes* EGD | 6.0 | 7.0 | 0.39 | 0.41 |
| Gram-negative | | | | |
| *E. coli* ML-35p | 0.64 | 1.2 | 5.0 | 2.2 |
| *E. coli* mcr 106 | 0.54 | 0.92 | 1.7 | 0.66 |
| *E. coli* BAS 894 | 0.41 | 1.3 | 0.17* | 0.46 |
| *S. typhimurium* 14028s | 0.72 | 2.7 | >200 | 1.9 |
| *S. typhimurium* 7953s | 0.43 | 1.1 | 0.22* | 1.2 |
| *K. pneumoniae* 2270 | 0.70 | 1.2 | >200 | 1.3 |
| *P. aeruginosa* SBI-N | 0.44 | 0.31 | 0.19* | 0.60 |
| *P. aeruginosa* MR 2133 | 0.51 | 0.44 | 0.29* | 0.91 |
| *P. aeruginosa* MR 3007 | 0.71 | 0.93 | 0.17* | 0.42 |

As shown, the clavanins are considerably more effective against certain Gram-positive bacteria than are Cecropin P1 or Magainin 1; all of the peptides, nevertheless, have wide-spectrum antimicrobial activity.

Figure 9B:
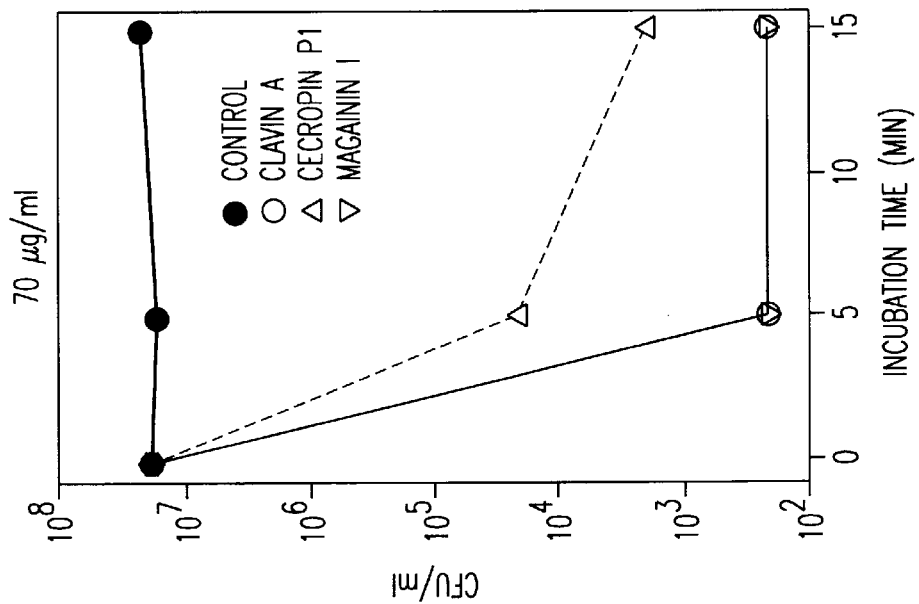
FIG. 9 shows the kinetics of Clavanin A, Clavanin A(K) and comparatively, Cecropin P1 and Magainin 1 in their antimicrobial action against L. monocytogenes.
Figure 9A:
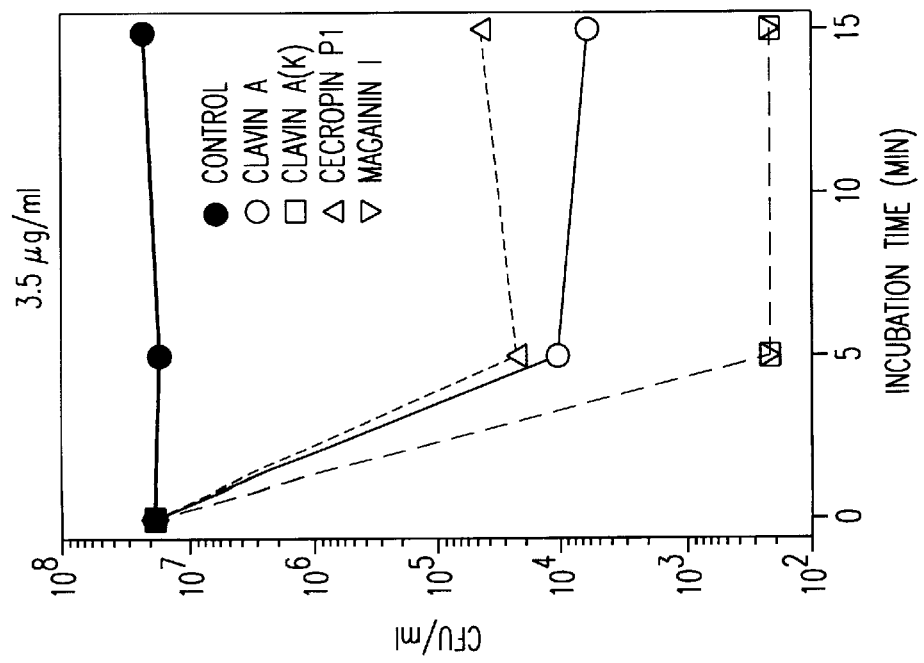

*E. coli* were 1.5 or 3.1 µg/ml. The results of these experiments are shown in FIGS. 9 and 10. Both Clavanin A and Clavanin A(K) have an antimicrobial effect after as little as 5 min at these concentrations.

It is claimed:

1. A recombinant expression system for production of an antimicrobial peptide having an α-helical conformation and the amino acid sequence $$X'_1 X_2 B'_3 X_4 X_5 U_6 B_7 X_8 X_9 B_{10} B_{11} X_{12} U_{13} Z_{14} \text{-} X_{15} X_{16} B^*_{17} U_{18} X_{19} U_{20} B_{21} X_{22} X_{23}$$ (1) (SEQ ID NO:1)

including the salts, esters, amides and acylated forms thereof,
wherein
$X'_1$ is Val, Leu, Ile, or Ala;
$X_2$ is Phe, Trp or Tyr;
$B'_3$ is Asn, Gln, His, Lys or Arg;
$X_4$ and $X_5$ is each independently selected from the group consisting of Phe, Leu, Tyr, and Val;
$U_6$ is Gly, Ser or Ala;
$B_7$ is Lys or Arg;
$X_8$ and $X_9$ is each independently selected from the group consisting of Ile, Leu and Val;
$B_{10}$ and $B_{11}$ is each independently His, Lys or Arg;
$X_{12}$ is Val, Ile, or Leu;
$U_{13}$ is Ala, Ser or Gly;
$Z_{14}$ is Asn or Gln;

$X_{15}$ and $X_{16}$ is each independently selected from the group consisting of Phe, Tyr, Trp, Val, Leu and Ile;

$B^*_{17}$ is His, Lys, Arg, Trp, Phe or Tyr or a modified form thereof;

$U_{18}$ is Ala, Ser or Gly;

$X_{19}$ is Phe, Tyr or Trp;

$U_{20}$ is Gly, Ala or Ser;

$B_{21}$ is His, Lys or Arg; and each of $X_{22}$ and $X_{23}$ is Ile, Val, Leu, Phe, Tyr or Trp, which expression system comprises a nucleotide sequence encoding said peptide operably linked to control sequences for effecting expression.

2. The recombinant expression system of claim 1 wherein the nucleotide sequence encodes a precursor peptide.

3. A recombinant host cell modified to contain the expression system of claim 1.

4. A method to produce an antimicrobial peptide which method comprises culturing the modified host cells of claim 3 under conditions wherein said peptide is produced.

* * * * *